(12) United States Patent
Reves et al.

(10) Patent No.: US 12,329,430 B2
(45) Date of Patent: Jun. 17, 2025

(54) BONE MATERIAL DISPENSING SYSTEM AND METHODS OF USE

(71) Applicant: Warsaw Orthopedic, Inc., Warsaw, IN (US)

(72) Inventors: Benjamin T. Reves, Memphis, TN (US); Joseph Thomas Hirsch, Memphis, TN (US); Mark R. Grizzard, Munford, TN (US); Daniel A. Shimko, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 817 days.

(21) Appl. No.: 17/379,545

(22) Filed: Jul. 19, 2021

(65) Prior Publication Data

US 2023/0019406 A1 Jan. 19, 2023

(51) Int. Cl.
*A61B 17/88* (2006.01)
*A61B 17/00* (2006.01)

(52) U.S. Cl.
CPC ...... *A61B 17/8811* (2013.01); *A61B 17/8816* (2013.01); *A61B 17/8819* (2013.01); *A61B 17/8822* (2013.01); *A61B 2017/00477* (2013.01)

(58) Field of Classification Search
CPC ........... A61F 2/4601; A61F 2002/4627; A61B 17/8833
See application file for complete search history.

(56) References Cited

U.S. PATENT DOCUMENTS

| | | | |
|---|---|---|---|
| 3,255,570 A | 6/1966 | Weimer | |
| 3,598,293 A | 8/1971 | Lee | |
| 4,338,925 A | 7/1982 | Miller | |
| 5,433,256 A | 7/1995 | Vasers | |
| 5,588,745 A | 12/1996 | Tanaka et al. | |
| 6,196,426 B1 | 3/2001 | White | |
| 6,364,519 B1 | 4/2002 | Hughes et al. | |
| 6,439,439 B1 | 8/2002 | Richard et al. | |
| 6,582,438 B2 | 6/2003 | DeMayo | |

(Continued)

FOREIGN PATENT DOCUMENTS

| | | |
|---|---|---|
| CN | 2047799918 | 11/2015 |
| CN | 105147386 | 12/2015 |

(Continued)

OTHER PUBLICATIONS

Extended European Search Report issued Nov. 15, 2022 by the European Patent Office in corresponding European patent application No. 22179388.8.

*Primary Examiner* — Anu Ramana

(74) *Attorney, Agent, or Firm* — Sorell, Lenna & Schmidt, LLP

(57) ABSTRACT

A bone material dispensing system is provided. The bone material dispensing system comprises a funnel having a proximal portion, the proximal portion comprising a top end and a bottom end, the top end opposite the bottom end, the top end comprising a surface having a protrusion configured to receive a locking member of a bone material dispensing device and the bottom end comprising a connector configured to secure the funnel to the bone material dispensing device. A bone material dispensing system comprises a pusher and a holder is provided. A method of dispensing bone material with the bone material dispensing system is also provided.

13 Claims, 12 Drawing Sheets

(56) References Cited

U.S. PATENT DOCUMENTS

| | | | |
|---|---|---|---|
| 7,011,238 B1 | 3/2006 | Sung | |
| 7,316,689 B2 | 1/2008 | Lieberman | |
| 8,529,576 B2 * | 9/2013 | Krueger | A61B 17/8819 606/86 R |
| 8,685,031 B2 | 4/2014 | Kleiner et al. | |
| 8,721,600 B2 * | 5/2014 | Henniges | B01F 31/40 604/209 |
| 8,795,365 B2 | 8/2014 | Arcenio et al. | |
| 8,845,646 B2 | 9/2014 | Vendrely et al. | |
| 8,900,620 B2 | 12/2014 | Fulmer et al. | |
| 9,033,994 B2 | 5/2015 | Fingerhut | |
| 9,101,475 B2 | 8/2015 | Wei et al. | |
| 9,101,606 B2 | 8/2015 | Drapeau et al. | |
| 9,220,598 B2 | 12/2015 | Betz et al. | |
| 9,333,082 B2 | 5/2016 | Wei et al. | |
| 9,394,152 B2 | 7/2016 | Connellan et al. | |
| 9,492,278 B2 | 11/2016 | Wei et al. | |
| 10,195,053 B2 * | 2/2019 | Kleiner | A61F 2/4611 |
| 10,687,880 B2 * | 6/2020 | Deridder | A61B 17/8808 |
| 11,364,062 B2 * | 6/2022 | Flores | A61B 17/8822 |
| 2002/0092871 A1 | 7/2002 | Richard et al. | |
| 2002/0112981 A1 | 8/2002 | Cooper et al. | |
| 2004/0193170 A1 | 9/2004 | Kemppainen et al. | |
| 2005/0155901 A1 | 7/2005 | Kreuger et al. | |
| 2009/0318925 A1 | 12/2009 | Campion et al. | |
| 2010/0094307 A1 | 4/2010 | Evans et al. | |
| 2010/0179507 A1 | 7/2010 | Hess et al. | |
| 2011/0015640 A1 | 1/2011 | Hess et al. | |
| 2011/0054408 A1 | 3/2011 | Wei et al. | |
| 2011/0060227 A1 | 3/2011 | Saadat | |
| 2012/0065613 A1 | 3/2012 | Pepper et al. | |
| 2014/0257232 A1 | 9/2014 | Mathur et al. | |
| 2014/0263389 A1 | 9/2014 | Perozek et al. | |
| 2014/0324013 A1 | 10/2014 | Shadeck et al. | |
| 2015/0112352 A1 | 4/2015 | Kraus et al. | |
| 2016/0038207 A1 | 2/2016 | Wei et al. | |
| 2016/0250038 A1 | 9/2016 | Wei et al. | |
| 2016/0288161 A1 | 10/2016 | Yi | |
| 2018/0125558 A1 | 5/2018 | Flores et al. | |
| 2018/0250145 A1 | 9/2018 | Stevenson et al. | |

FOREIGN PATENT DOCUMENTS

| | | |
|---|---|---|
| EP | 2865341 | 4/2015 |
| WO | 2004/100771 A2 | 11/2004 |
| WO | 2012/151253 | 11/2012 |
| WO | 2013/014505 | 1/2013 |
| WO | 2015/132034 | 9/2015 |
| WO | 2019/040851 | 2/2019 |
| WO | 2020/009882 A1 | 1/2020 |

* cited by examiner

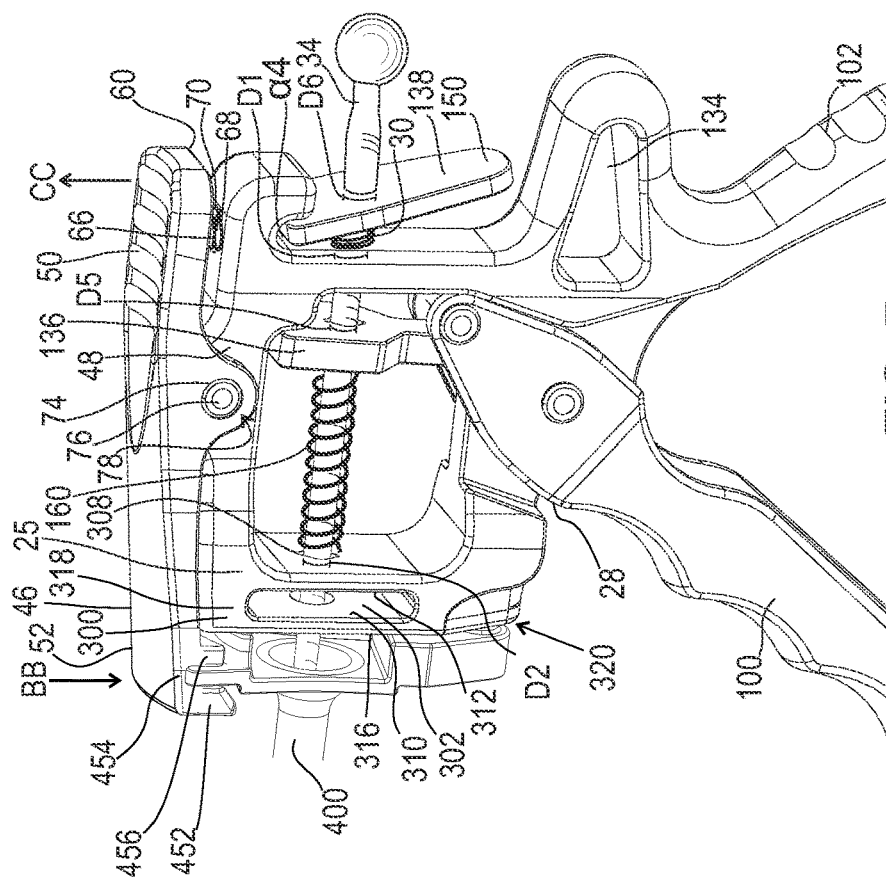

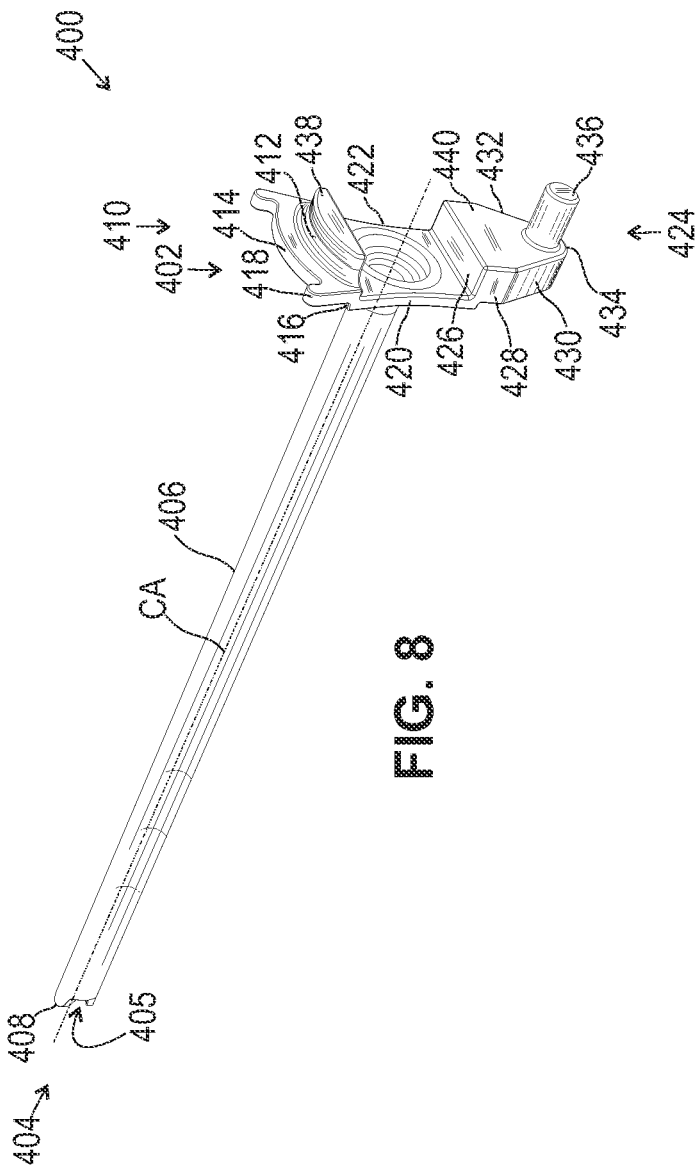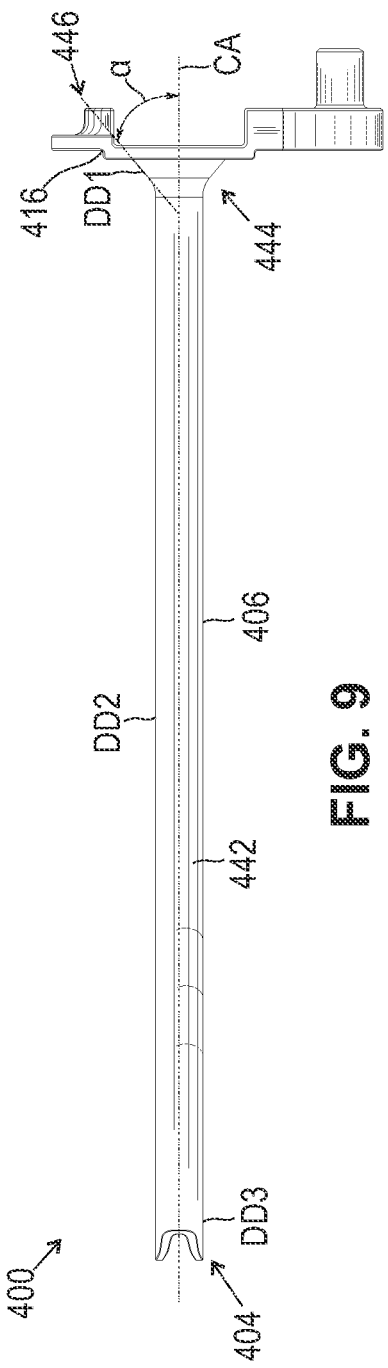

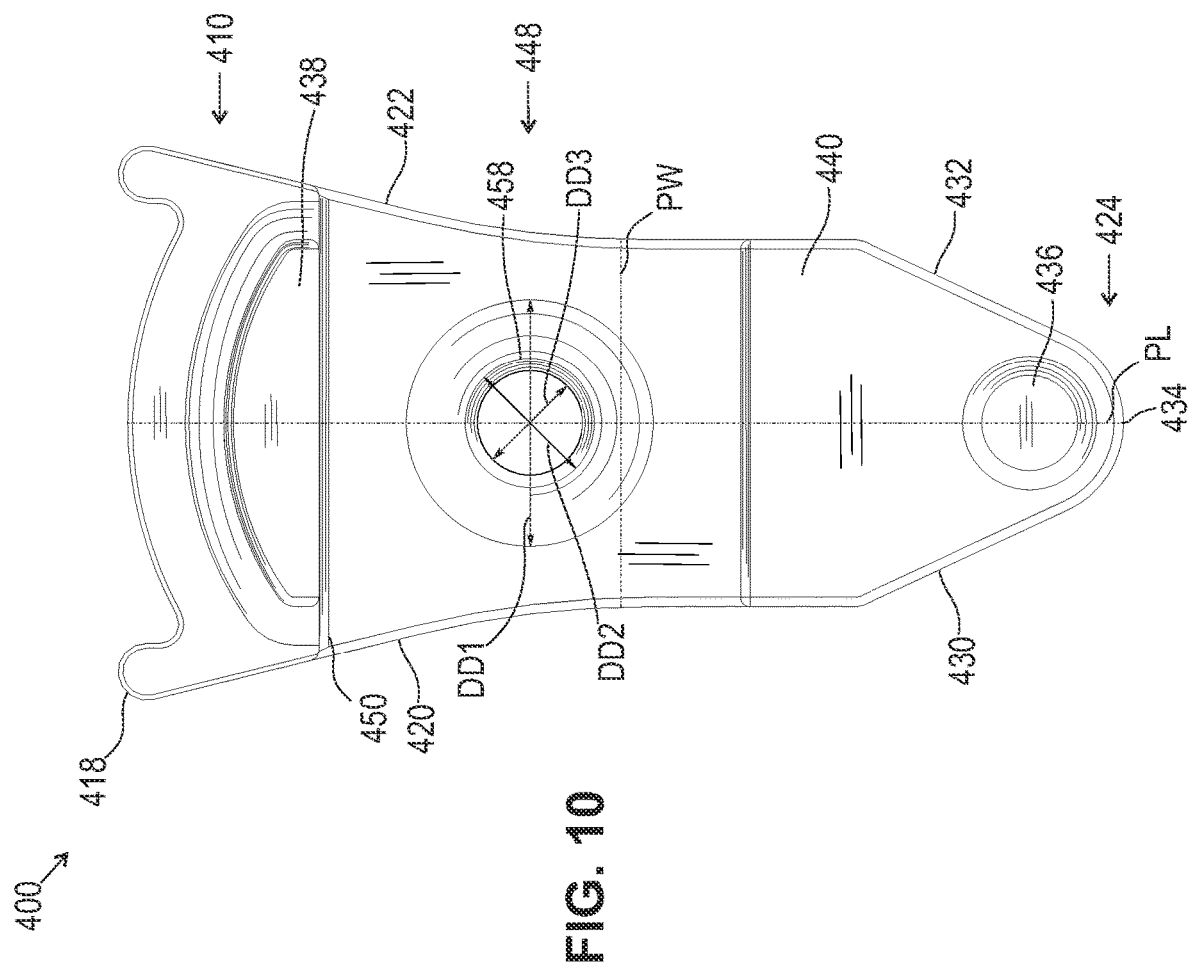

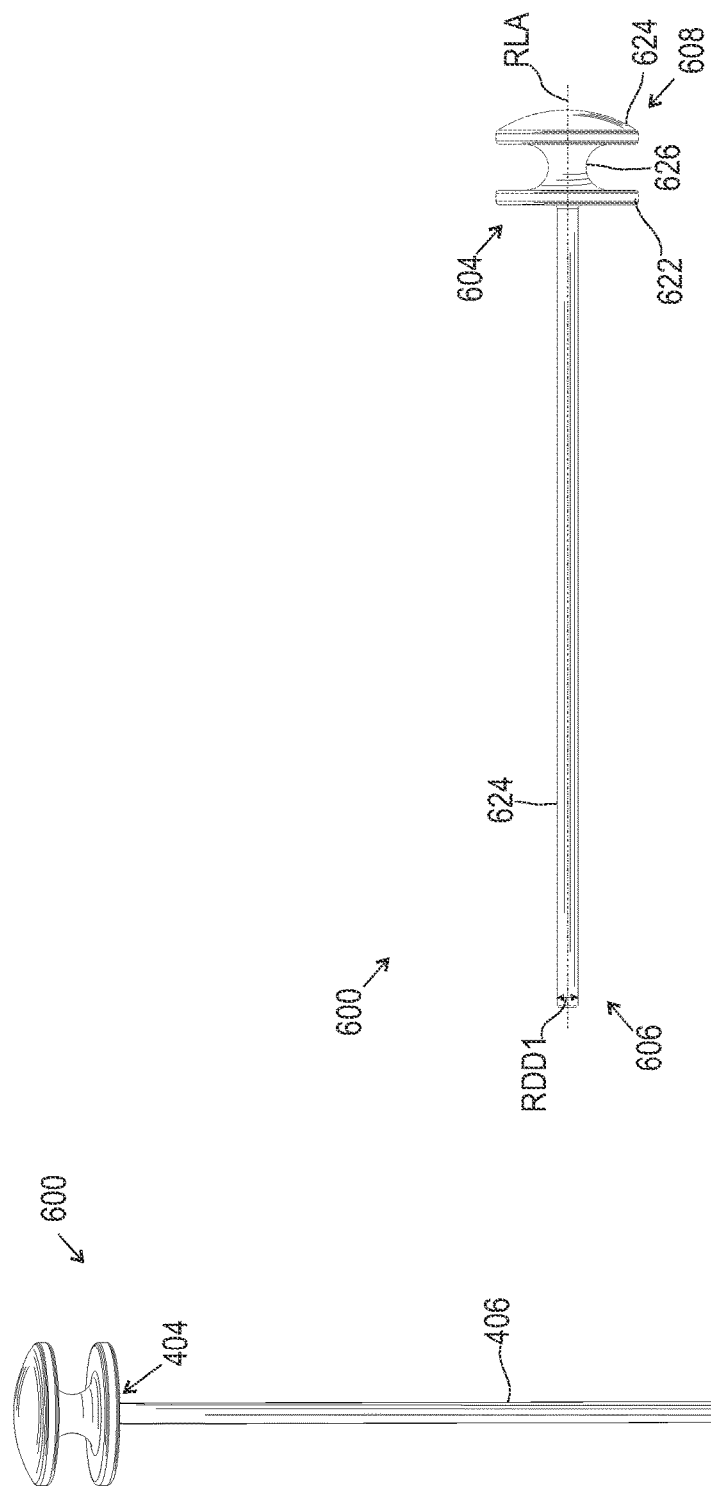

BONE MATERIAL DISPENSING SYSTEM AND METHODS OF USE

BACKGROUND

Various devices and methods have been used to administer bone material, such as bone graft, to a surgical site. Bone graft is important in orthopedic procedures for the repair of bone defects caused by injury, disease, wounds, or surgery. Toward this end, a number of materials have been used or proposed for use in the repair of bone defects. The biological, physical, and mechanical properties of the materials are among the major factors influencing their suitability and performance in various orthopedic applications.

Conventionally, bone tissue regeneration is achieved by filling a bone defect with a bone material, for example, a bone graft. Over time, the bone graft is incorporated by the host and new bone remodels the bone graft. Bone material can include bone from the patient's own body, synthetic bone material, natural substitute bone material or combinations thereof.

To deliver the bone material to the bone defect, oftentimes the bone material is mixed with liquid or a therapeutic agent, powder, fiber or granular material. Further, transfer of bone material to the dispensing device is often done by crude and messy packing of the bone dispensing device which can cause unwanted waste and spillage of bone material. During transfer and delivery of the bone material, these devices can also increase the risk of contamination of the bone material. Additionally, some dispensing devices can cause damage to surrounding tissue of a surgical site during administration of the bone material. Moreover, bone material can clog certain dispensing devices due to its consistency and/or due to the design of the dispensing device and the amount of bone material cannot be controlled effectively when this occurs. Some dispensing devices have a bulky surface for dispensing the bone material. However, this bulky surface may make it more difficult to maneuver the device and more accurately dispense the bone material.

It would therefore be desirable to provide a bone material dispensing system that includes a reusable bone material dispensing device that allows easier loading of the bone material, which reduces the risk of contamination and spillage of bone material from the dispensing device. It would be beneficial to provide a dispensing device and a funnel that reduce clogging during dispensing of the bone material and are also able to deliver the bone material incrementally in controlled amounts to a bone defect. It would be also beneficial to provide a dispensing device that has a light frame, a slim profile, and the ability to accurately dispense bone material so as to reduce wastage of the bone material. It would also be useful to provide a dispensing system including a kit having a pusher and a holder for the funnel to retrieve or dispense bone material from the clogged funnel during or after dispensing of the bone material.

SUMMARY

A funnel that reduces clogging during dispensing of bone material is provided. The funnel is able to deliver the bone material incrementally in controlled amounts to a bone defect. In some embodiments, a pusher is provided to allow dispensing and/or recovery of clogged or undispensed bone material that remains in the funnel. In some embodiments, a holder is provided to facilitate a stable platform to support the funnel, the dispensing system can also have a pusher to dispense the bone material from the funnel.

In some embodiments, there is a bone material dispensing system comprising a funnel having a proximal portion, the proximal portion comprising a top end and a bottom end, the top end opposite the bottom end, the top end comprising a surface having a protrusion configured to receive a locking member of a bone material dispensing device and the bottom end comprising a connector configured to secure the funnel to the bone material dispensing device.

In some embodiments, there is a bone material dispensing system comprising a funnel having a proximal portion, the proximal portion comprising a top end and a bottom end, the top end opposite the bottom end, the top end comprising a surface having a protrusion configured to receive a locking member of a bone material dispensing device and the bottom end comprising a connector configured to secure the funnel to the bone material dispensing device; a pusher having a shaft and a head, the shaft having a diameter smaller than a diameter of the funnel body at least a portion of the pusher configured to slidably move within the funnel; and a holder configured to receive the proximal portion of the funnel.

In some embodiments, there is a method of dispensing a bone material, the method comprising loading bone material into a bone material dispensing system, the bone material dispensing system comprising a funnel having a proximal portion, the proximal portion comprising a top end and a bottom end, the top end opposite the bottom end, the top end comprising a surface having a protrusion configured to receive a locking member of a bone material dispensing device and the bottom end comprising a connector configured to secure the funnel to the bone material dispensing device.

In some embodiments, there is a method of dispensing a bone material provided. The method comprises loading a bone material dispensing device with the bone material, the bone material dispensing device comprising a housing having a frame comprising an opening configured to slidably receive at least a portion of a plunger, a locking member pivotably connected to the housing, the locking member comprising a locking surface extending adjacent to the housing configured to engage a surface of a funnel, the frame comprising a contact surface and a front opening configured to engage a funnel, engaging a connector of the funnel with the front opening of the frame and the locking member being movable in a locking position, such as a downward position to lock the surface of the funnel to the housing, the surface having a protrusion stabilizing the locking member, aligning the funnel with the frame and the funnel configured to receive at least a portion of the plunger to dispense the bone material.

While multiple embodiments are disclosed, still other embodiments of the present disclosure will become apparent to those skilled in the art from the following detailed description. As will be apparent, the disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE FIGURES

In part, other aspects, features, benefits and advantages of the embodiments will be apparent with regard to the following description, appended claims and accompanying figures.

FIG. 6 is an enlarged perspective view of a portion of the bone material dispensing device of FIG. 2 with the housing, locking member shown in the release position, also shown are second and third biasing members and plunger.

FIG. 7 is an enlarged perspective view of a portion of the bone material dispensing device of FIG. 2 with the housing, locking member shown in the locked position, also shown are second and third biasing members and plunger.

FIG. 8 is a perspective view of the funnel of FIG. 1.

FIG. 9 is a side view of the funnel of FIG. 1.

FIG. 10 is a front view of the funnel of FIG. 1.

FIG. 11 is an assembled view of the funnel, the holder and the pusher of FIG. 1. A pusher is inserted into the funnel's distal portion and the funnel's proximal portion is sitting on a contact surface of the holder.

FIG. 12 is a side view of the pusher in FIG. 1. The pusher includes a head, a shaft and a longitudinal axis extending from a proximal portion to a distal portion of the pusher.

Figure 1:
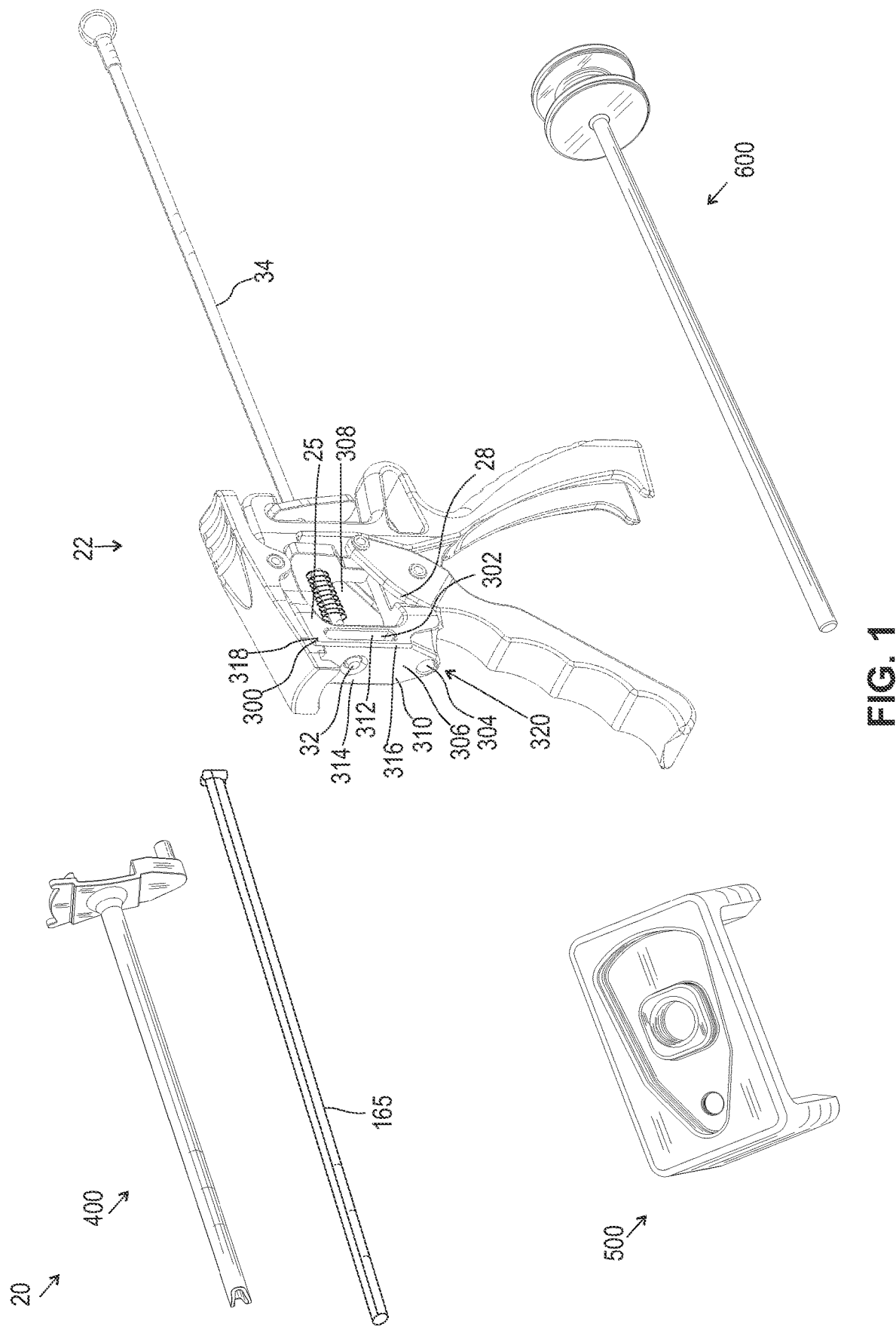
FIG. 1 is a perspective view of a bone material dispensing system according to an aspect of the present application. The bone material dispensing system comprises a bone material dispensing device, a funnel, a folding cannula, a holder and a pusher. The holder is engageable with the funnel for retrieving/dispensing the bone material from the funnel using the pusher.

It is to be understood that the figures are not drawn to scale. Further, the relation between objects in a figure may not be to scale and may, in fact, have a reverse relationship as to size. The figures are intended to bring understanding and clarity to the structure of each object shown, and thus, some features may be exaggerated in order to illustrate a specific feature of a structure.

DETAILED DESCRIPTION

Definitions

It is noted that, as used in this specification and the appended claims, the singular forms "a," "an," and "the," include plural referents unless expressly and unequivocally limited to one referent.

The term "allograft" refers to a graft of tissue obtained from a donor of the same species as, but with a different genetic make-up from, the recipient, as a tissue transplant between two humans.

The term "autologous" refers to being derived or transferred from the same individual's body, such as for example an autologous bone marrow transplant.

The term "xenograft" refers to tissue or organs from an individual of one species transplanted into or grafted onto an organism of another species, genus, or family.

The term "mammal" refers to organisms from the taxonomy class "mammalian," including, but not limited to, humans; other primates, such as chimpanzees, apes, orangutans and monkeys; rats, mice, cats, dogs, cows, horses, etc.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "bone material" includes natural and/or inorganic material such as, for example, inorganic ceramic and/or bone substitute material. The bone material can also include natural bone material such as, for example, bone which is cortical, cancellous or cortico-cancellous of autogenous, allogenic, xenogenic, or transgenic origin. In some embodiments, bone material can include demineralized bone material such as, for example, substantially demineralized bone material, partially demineralized bone material, or fully demineralized bone material.

"Demineralized" as used herein, refers to any material generated by removing mineral material from tissue, e.g., bone tissue. In certain embodiments, the demineralized compositions described herein include preparations containing less than 5% calcium and preferably less than 1% calcium by weight. Partially demineralized bone (e.g., preparations with greater than 5% calcium by weight but containing less than 100% of the original starting amount of calcium) is also considered within the scope of the application. In some embodiments, demineralized bone has less than 95% of its original mineral content.

In some embodiments, demineralized bone has less than 95% of its original mineral content. In some embodiments, demineralized bone has less than 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6 and/or 5% of its original content. In some embodiments, "demineralized" is intended to encompass such expressions as "substantially demineralized," "superficially demineralized," "partially demineralized," "surface demineralized," and "fully demineralized."

"Partially demineralized" is intended to encompass "surface demineralized." "Partially demineralized bone" is intended to refer to preparations with greater than 5% calcium by weight but containing less than 100% of the original starting amount of calcium. In some embodiments, partially demineralized comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% of the original starting amount of calcium.

In some embodiments, the demineralized bone may be surface demineralized from about 1-99%. In some embodiments, the demineralized bone is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% surface demineralized. In various embodiments, the demineralized bone may be surface demineralized from about 15-25%. In some embodiments, the demineralized bone is 15, 16, 17, 18, 19, 20, 21, 22, 23, 24 and/or 25% surface demineralized.

"Superficially demineralized" as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context.

"Demineralized bone matrix" as used herein, refers to any material generated by removing mineral material from bone tissue. In preferred embodiments, the DBM compositions as used herein include preparations containing less than 5% calcium and preferably less than 1% calcium by weight.

"Biocompatible" as used herein, refers to materials that, upon administration in vivo, do not induce undesirable long-term effects.

"Osteoconductive" as used herein, refers to the ability of a non-osteoinductive substance to serve as a suitable template or substance along which bone may grow.

"Osteogenic", as used herein, refers to the ability of an agent, material, or implant to enhance or accelerate the growth of new bone tissue by one or more mechanisms such as osteogenesis, osteoconduction, and/or osteoinduction.

"Osteoinductive" as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference.

The terms "upper", "lower", "top", "bottom", "side", "proximal", "distal" and so forth have been used herein merely for convenience to describe the present invention and its parts as oriented in the drawings. It is to be understood, however, that these terms are in no way limiting to the disclosure since the dispensing systems described herein may obviously be disposed in different orientations when in use.

The term "removably engage" includes engagement of two or more components that can be used or combined into one element via the engagement of the two or more elements with a connecting means, a locking means, or by placing the elements tightly together. The two or more elements may be positioned adjacent to each other and each include a contacting surface.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention is an approximation; the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the disclosure, examples of which are illustrated in the accompanying figures. While the disclosure will be described in conjunction with the illustrated embodiments, it will be understood that they are not intended to limit the disclosure to those embodiments. On the contrary, the disclosure is intended to cover all alternatives, modifications, and equivalents that may be included within the disclosure as defined by the appended claims.

The headings below are not meant to limit the disclosure in any way; embodiments under any one heading may be used in conjunction with embodiments under any other heading.

Dispensing System

A bone material dispensing system 20, as shown in FIGS. 1-7 is provided that includes a reusable bone material dispensing device 22 that allows easier loading of bone material, reducing the risk of contamination and spillage of bone material from the bone material dispensing device. The system also has a delivery funnel 400 that substantially encloses the bone material to ease loading the bone material into the device and ease dispensing of the loaded bone material from the funnel to reduce or eliminate clogging and reduce or eliminate resistance when the bone material is dispensed. The system also has a cannula 165 that encloses the bone material allowing the bone material to be packed when loaded to the funnel, as described herein. The system can also have a pusher 600 that can be inserted into the funnel to dispense or remove the bone material from the funnel, as described herein. The system can also have a holder 500 that serves as a platform to hold the funnel in an upright position allowing the pusher to push the bone material with ease, as described herein.

The reusable bone material dispensing device administers bone material to a surgical site in incremental amounts. The bone material dispensing device can be a bone material dispensing device that reduces the risk of contamination and spillage of bone material from the dispensing device and administers the bone material to a surgical site (e.g., bone defect) while reducing damage to surrounding tissue. The bone material dispensing device reduces clogging and allows incremental dispensing of the bone material. The bone material dispensing device is also configured for left handed and right handed use. A surgical site can include, but is not limited to, injury defects brought about during the course of surgery, infection, malignancy or developmental malformation. Specific bones which can be repaired or replaced with the bone material can include, but are not limited to, the ethmoid; frontal; nasal; occipital; parietal; temporal; mandible; maxilla; zygomatic; cervical vertebra; thoracic vertebra; lumbar vertebra; sacrum; rib; sternum; clavicle; scapula; humerus; radius; ulna; carpal bones; metacarpal bones; phalanges; ilium; ischium; pubis; femur; tibia; fibula; patella; calcaneus; tarsal and metatarsal bones. In some embodiments, the bone material dispensing device administers bone material to at least a portion of the spinal cord such as vertebrae or a vertebra.

Figure 2:
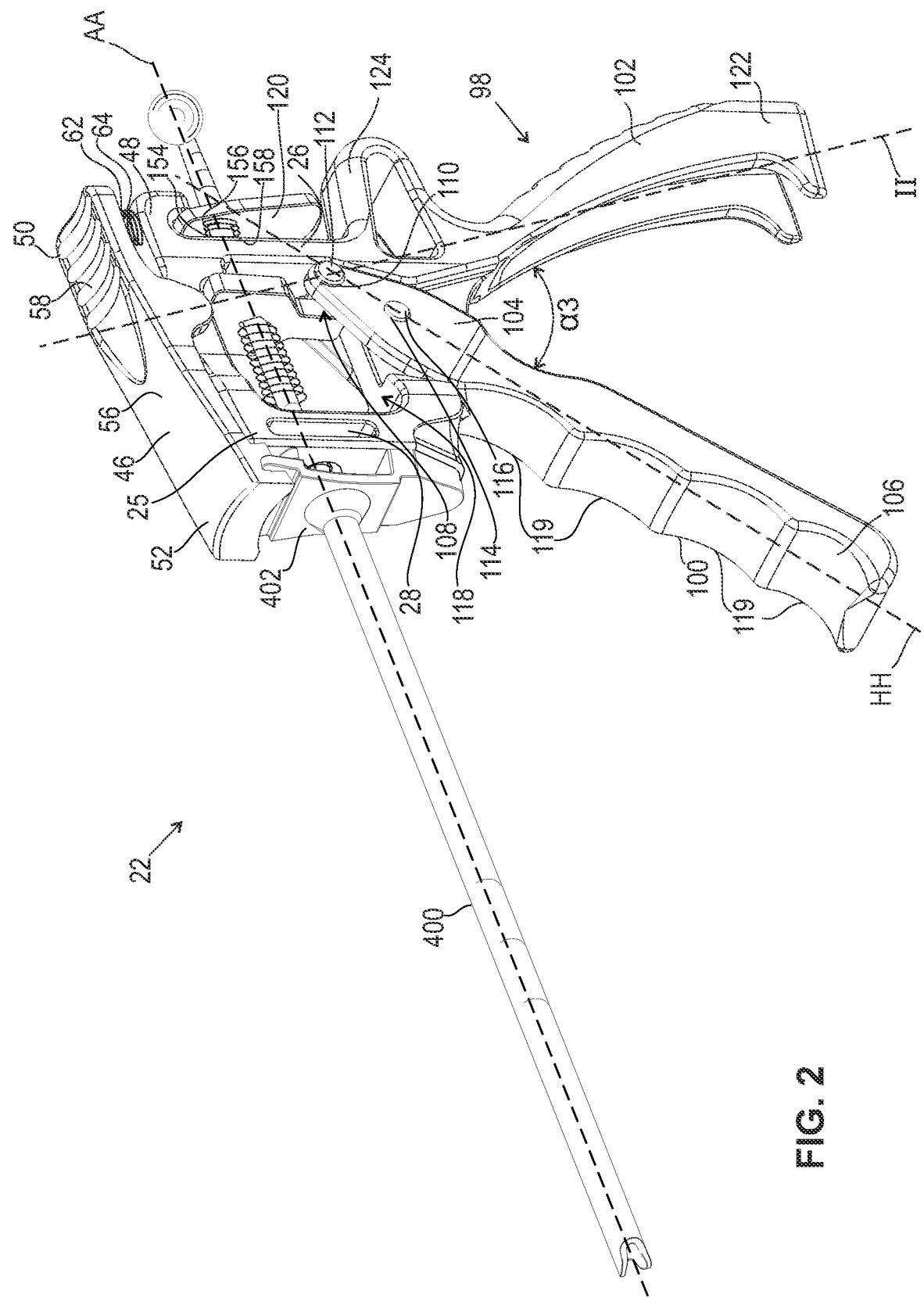
FIG. 2 is a perspective view of the bone material dispensing device according to an aspect of the present application. The bone material dispensing device includes a housing having a proximal end having a first opening, a distal end having a second opening, and a longitudinal axis. The first opening and the second opening are configured to slidably receive at least a portion of a plunger. The bone material dispensing device includes an optional locking member that is pivotably connected to an upper surface of the housing and extends transversely above the upper surface from at least the proximal end to the distal end of the housing. The locking member comprises a distal end configured to engage a portion of a funnel.
Figure 4:
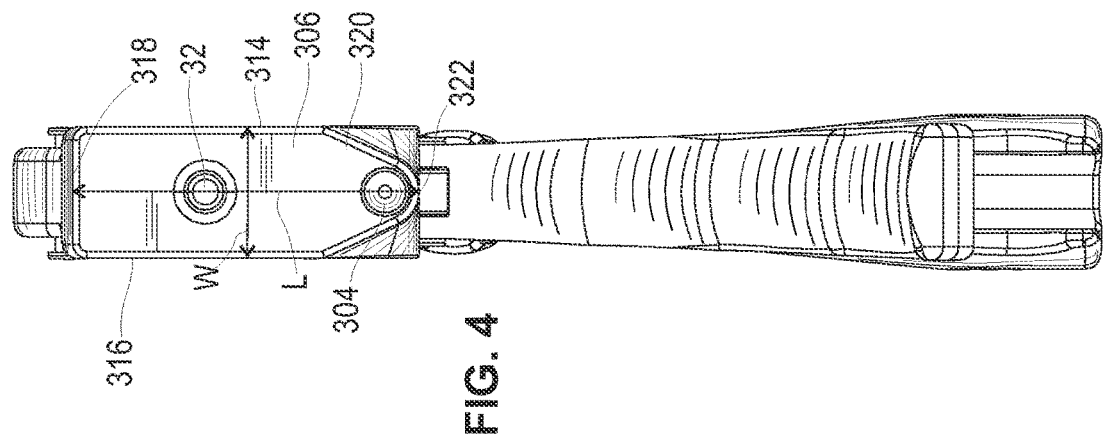
FIG. 4 is a front view without the locking member of the bone material dispensing device of FIG. 1. The bone material dispensing device includes a length extending from a top end to a distal end of a contact surface. The bone material dispensing device includes a width extending from a first edge to a second edge of a contact surface.
Figure 3:
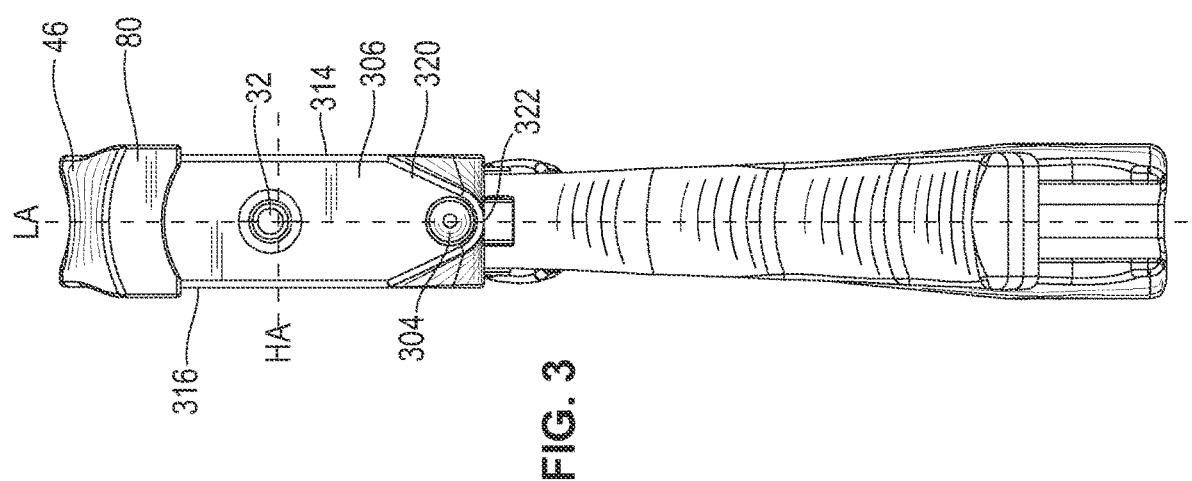
FIG. 3 is a front view of the bone material dispensing device of FIG. 1. The bone material dispensing device includes a longitudinal axis extending in a direction from a top end toward a distal end of a contact surface. The bone material dispending device includes a horizontal axis extending in a direction from a first edge to a second edge of the contact surface.

The bone material dispensing device includes a housing 25 having a proximal end 26, a distal end 28, and a longitudinal axis AA disposed therebetween, as shown in FIG. 2. The proximal end of the housing includes a first opening 30 and the distal end includes a second opening 32, as shown in FIG. 6. The first opening and the second opening are configured to slidably receive at least a portion of a plunger 34, as described herein. The distal end 28 of the housing comprises a distal frame body or a frame 300. The distal frame is monolithic with the housing. The frame comprises a front wall 310, a back wall 312, a frame opening or an air gap 302. The front wall is disposed away from the proximal end of the housing and is configured to contact a funnel 176. The back wall is disposed closer to the proximal end of the housing. The back wall comprises a back opening 308 configured to receive the plunger. The air gap is disposed between the front wall and the back wall. The air gap comprises a generally rectangular profile with a longer length along a length L of the frame, as shown in FIG. 4. In some embodiments, the length of the frame extends from a top end 318 to a tapered end 320 of the frame along a longitudinal axis LA. The frame provides support to the plunger as it passes through the distal end of the housing while allowing the funnel to securely engage the contact surface 306 disposed on the front wall. In some embodiments, the contact surface has a generally flat surface comprising the second opening. In some embodiments, the second opening is larger than the back opening. In some embodiments, the contact surface further comprises a front opening 304. The front opening is disposed below the second opening, which is disposed adjacent to the tapered end. In some embodiments, the front opening is configured to receive a corresponding protrusion (not shown in figures) from the funnel. In some embodiments, the funnel does not contact and/or cover the front opening. The contact surface can be a tubular shape (e.g., oval, circular, etc.) or a non-tubular shape (e.g., rectangular, triangular, square, etc.). In some embodiments, the proximal end of the funnel is such that the funnel is only partially covered by the generally rectangular contact surface in the middle when the second opening is aligned with funnel passage 179, while other portions of the funnel are not covered by the contact surface, as shown in FIGS. 6 and 7. In some embodiments, the frame further comprises a top end and a tapered end opposing each other along the longitudinal axis, as shown in FIGS. 3 and 4. In some embodiments, the top end has a flat profile configured to match a bottom surface of a locking member 46. The tapered end has a shorter width than a width W of the frame, as shown in FIG. 4. In some embodiments, the width across the second opening is longer than the width across the tapered end, as shown in FIG. 3. In some embodiments, the front wall further comprises a first edge 314 and a second edge 316. In some embodiments, the width of the frame extends from the first edge to the second edge along a horizontal axis HA. In some embodiments, the first edge and the second edge extend from the top end to the tapered end. In some embodiments, the first edge and the second edge join at the tapered end at an apex 322 of the tapered end forming a triangular shape such that the front wall has a generally rectangular portion and a generally triangular portion. This configuration gives the device a slim profile so that the device is easier to maneuver and handle in use.

The first opening has a diameter D1 and the second opening has a diameter D2, as shown in FIG. 7. D1 and D2 are the same diameter. In some embodiments, D1 and D2 can have different diameters. In some embodiments, the diameters D1 and D2 can be from about 2 millimeters (mm) to about 40 mm. The diameters can be from about 2, 4, 6, 8, 10, 12, 14, 16, 18, 20, 22, 24, 26, 28, 30, 32, 34, 36, 38 to about 40 mm. The first and second openings can be shaped and can be round, oval, rectangular or square.

The plunger, as described herein, has a proximal end 36, a distal end 38 and a body 40 disposed therebetween. The plunger is configured to assist in the dispensing/administration of the bone material to a surgical site, as described herein. This allows for controlled and incremental administration of the bone material to the bone defect. The proximal end of the plunger includes a stopper 42 that is configured to prevent the plunger from passing entirely through the first and second openings of the housing when the plunger is translated in the direction of the distal end of the housing. In some embodiments, the stopper can be ball shaped and have a diameter that is greater than diameters D1 and D2. In some embodiments, the distal end of the plunger can include a tip 44 having various geometries and sizes that are tailored for various sized cannulas, as described herein, and/or for varying viscosities of bone material, as described herein. In some embodiments, the tip of the plunger can be square, rectangular, round, plug, or disc shaped.

Figure 5:
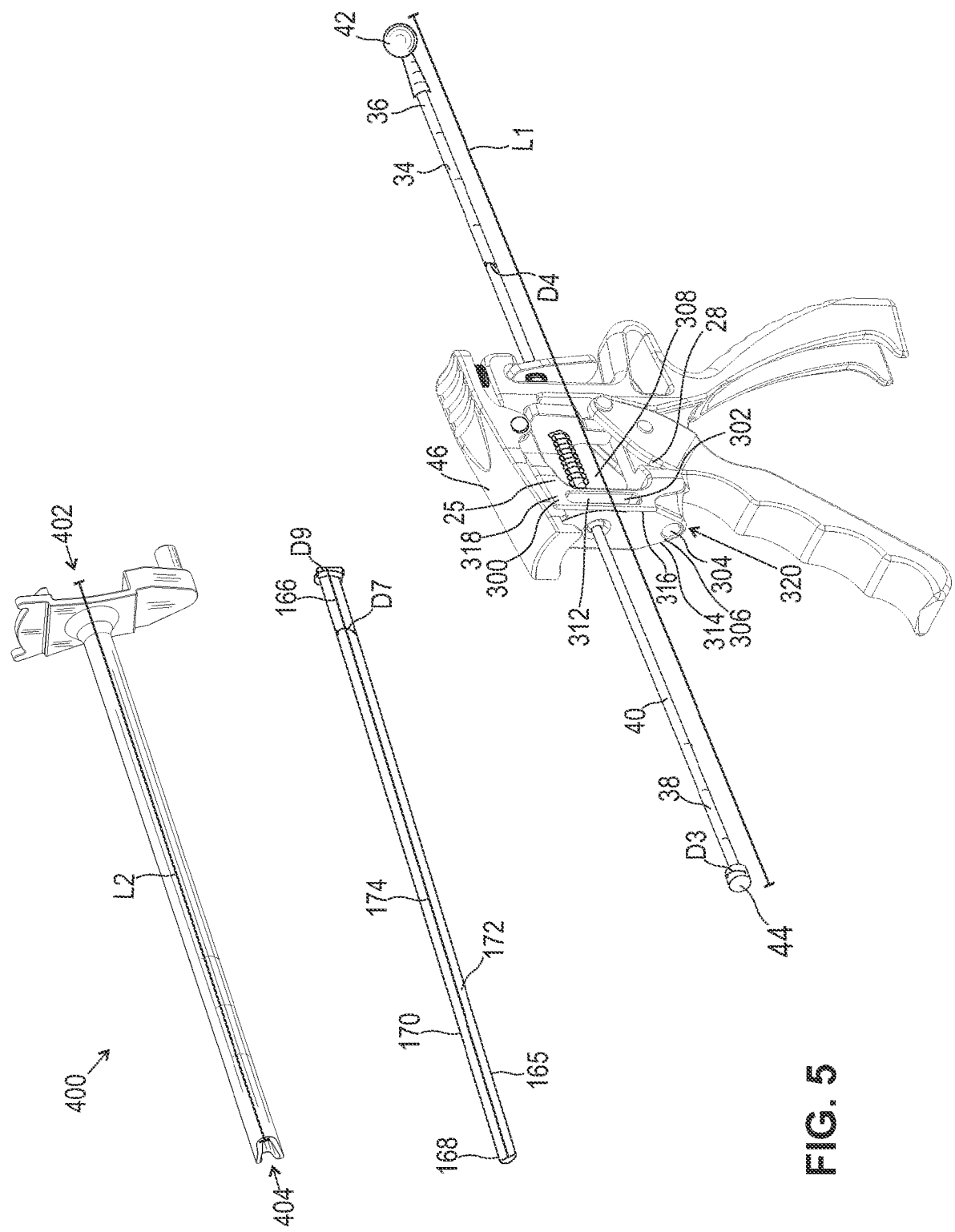
FIG. 5 is a perspective view of the bone material dispensing device of FIG. 2. The funnel and folding cannula are shown separated from the device.

The tip can have a diameter D3 and the body can have a diameter D4, as shown in FIG. 5. In some embodiments, diameter D3 is larger than diameter D4. In some embodiments, diameters D3 and D4 are the same size. Diameter D4 of the body of the plunger is smaller than diameters D1 and D2, and diameter D3 can be larger, the same or less than diameters D1 and D2. In some embodiments, the diameter D4 of the body of the plunger is slightly smaller than diameters D1 and D2 but allows at least a portion of the plunger to slide within the openings. In some embodiments, diameters D3 and D4 can be from about 2 millimeters (mm) to about 36 mm. The diameters D3 and D4 can be from about 2, 4, 6, 8, 10, 12, 14, 16, 18, 20, 22, 24, 26, 28, 30, 32, 34 to about 36 mm. The plunger can also have a certain length L1 of from about 1 to about 20 inches, as shown in FIG. 5. In some embodiments, the length L1 of the plunger can be from about 1, 2, 3, 4, 5, 6, 7, 8, 9, 10, 11, 12, 13, 14, 15, 16, 17, 18, 19 to about 20 inches. The plunger length can be smaller, larger or the same size as the cannula 165, as described herein. In some embodiments, the plunger can be flexible or rigid.

The bone material dispensing device includes a locking member 46. The locking member is configured to lock a portion of a funnel, as described herein, to the housing of the bone material dispensing device. The locking member is pivotably connected to an upper surface 48 of the housing and extends adjacent to the upper surface of the housing, as shown in FIGS. 2, 6 and 7. The locking member includes a proximal end 50 configured to engage with a biasing member, as described herein, and a distal end 52 configured to engage with a portion of the funnel and the top end of the frame, as described herein, and an intermediate portion 54 disposed therebetween configured to pivotably engage with a portion of the upper surface of the housing.

The locking member is movable in a locking position, such as a downward position, to lock the portion of the funnel with the housing, and the locking member is movable in an unlocking position, such as an upward position, to unlock the portion of the funnel from the housing, as described herein.

The proximal end of the locking member includes an outer surface 56 that includes, in some embodiments, a gripping surface 58 that provides a grip for a user when the user pushes downward on the proximal end of the locking member during use. An interior surface 60 of the locking member defines a stanchion 62 disposed at the proximal end that is configured for engagement with a first end 66 of a first resilient member, such as a first spring 64, as shown in FIGS. 2 and 7. A portion of the upper surface of the proximal end of the housing includes a recess 68 configured for engagement with a second end 70 of the first spring. The stanchion and the recess are configured for engagement with the first spring.

The intermediate portion of the locking member includes a pivot point 72 engaged with the upper surface of the housing. The pivot point includes an opening 74, a pin 76 and an opening 78 formed from a portion of the upper surface of the housing, as shown in FIGS. 6 and 7. The pin is configured for disposal within openings 74 and 78. In some embodiments, the pivot point pivots at an angle α1 of about 1 degree to about 30 degrees. In some embodiments, the pivot point pivots at an angle α1 of about 1, 2, 3, 4, 5, 6, 7, 8, 9, 10, 11, 12, 13, 14, 15, 16, 17, 18, 19, 20, 21, 22, 23, 24, 25, 26, 27, 28, 29 to about 30 degrees.

The distal end of the locking member includes a locking surface, such as a flange 80 that extends adjacent to the distal end of the housing. The flange locks a portion of the funnel with the housing of the bone material dispensing device. As shown in FIG. 6, the flange can include an inner surface that is grooved 82 to facilitate engagement with a portion of the funnel.

The flange at the distal end of the locking member is moved in a downward position to lock the portion of the funnel with the housing, as shown by arrow BB in FIG. 7. When the flange is in the downward position, the proximal end is positioned in an upward direction, as shown by arrow CC. In this configuration, the first spring is partially compressed with the stored energy applying constant force against both stanchion 62 and recess 68. In some embodiments, the flange comprises three contacting surfaces forming n-shaped tongs to contact and secure the delivery funnel. A first contact surface 452, a second contact surface 454 and a third contact surface 456 are shown in FIG. 7. The flange unlocks the funnel when the flange is moved in an upward position, as shown by arrow DD in FIG. 6, when the user pushes the proximal end of the locking member in a downward direction, as shown by arrow EE. In this configuration, the first spring is further compressed and energy is stored for use when the locking member is moved again in the downward position, as described above.

The housing includes a trigger assembly 98, as shown in FIG. 2, that is configured to allow incremental slidable movement of the plunger to dispense the bone material, as described herein. The trigger assembly includes a driving handle 100 and a stationary handle 102. The driving handle includes a proximal end 104, a distal end 106 and a longitudinal axis HH disposed therebetween. The proximal end of the driving handle is configured for pivotable engagement with an intermediate portion of the stationary handle and a proximal end of a driving pawl, as described below. The proximal end of the driving handle includes a cavity 108, as shown in FIGS. 2 and 4. The cavity is configured for movable engagement with a portion of the driving pawl, as described herein.

The proximal end of the driving handle and transverse to the cavity includes a recess 110. The recess is configured for engagement with a pin 112 such that the proximal end of the driving handle pivotably engages with a portion of the driving pawl, as described herein. The proximal end of the driving handle includes a recess 114, as shown in FIG. 2. The recess is configured for engagement with a pin 116 such that the proximal end of the driving handle is movably engaged with a portion of the housing. The housing includes a recess 118 configured to engage with pin 116.

A surface of the driving handle includes gripping surfaces 119. The gripping surfaces are configured for engagement with a user's hand such that the driving handle can be controlled effectively by the user. The gripping surfaces can be raised, curved or straight. The gripping surfaces can also be roughened to increase the control that the user has over the driving handle.

The user moves the driving handle in the direction of the stationary handle. The driving handle engages the active pawl, which slides the plunger longitudinally and incrementally in the direction of the distal end. This allows for bone material to be incrementally dispensed from the bone material dispensing device.

The stationary handle includes a proximal end 120, a distal end 122, an intermediate portion 124 and a longitudinal axis II disposed between the proximal end and the distal end. The proximal end of the stationary handle includes a first side 126, a second side 128 and a third side 130, as shown in FIGS. 6 and 9. The first, second and third sides are part of the housing. The proximal end of the stationary handle can be monolithic with the housing and the first, second and third sides can be monolithic or fixed to the stationary handle. The intermediate portion of the stationary handle can be monolithic with the housing, and the intermediate portion can be inserted into the cavity of the driving handle. The second side includes a slot 132 that is configured for engagement with a portion of a passive pawl, as described herein and shown in FIG. 4. In some embodiments, the stationary handle and the housing are monolithic with one another. In some embodiments, the stationary handle and the housing are not monolithic.

The intermediate portion of the stationary handle is configured for engagement with the proximal end of the driving handle. The driving handle pivots towards and away from the stationary handle at an angle α3 from about 1 to about 60 degrees, shown in FIG. 2. In some embodiments, α3 is from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 to about 60 degrees.

The stationary handle defines one or more cutouts 134, as shown in FIG. 7. The cutouts can be oval, round, square, triangular, rectangular or any other regular or irregular shape. There can be one or more cutouts formed from the surface of the stationary handle, such as 1, 2, 3, 4, 5, 6 or more cutouts.

The trigger assembly of the housing further includes a driving pawl 136 and a passive pawl 138, as shown in FIGS. 6 and 7. The driving pawl is configured to work in conjunction with a resilient member to assist the stationary handle and the driving handle in incremental slidable movement of the plunger such that the plunger dispenses the bone material. In the embodiment shown in FIG. 6, the resilient member shown as a spring is concentric with the plunger. On movement of the driving handle to the stationary handle, pawl 136 engages plunger 34 and pushes the plunger longitudinally in increments while simultaneously compressing the spring. The driving pawl is disposed at one end of the resilient member and the other end of the resilient member is biased against the housing and plunger. Once the driving handle is released, the stored energy in the spring returns the driving handle and pawl longitudinally to their original positions.

The driving pawl includes a first end 140 and a second end 142, as shown in FIG. 4. The first end of the driving pawl is configured for movable engagement within the cavity of the driving handle. Recess 110 and a recess 144 disposed within the first end of the driving pawl, engage with pin 112 such that the proximal end of the driving handle pivotable engages with the first end of the driving pawl. The driving pawl includes a third opening 146 that is in alignment and in between the first opening and the second opening of the housing, as shown in FIGS. 3 and 4. The third opening is configured to slidably receive at least a portion of the plunger, as described herein. The third opening can be centrally located on the driving pawl.

The third opening has a diameter D5, as shown in FIG. 7. D5 can be the same diameter as D1 and D2, and D5 has a greater diameter than plunger diameter D4. In some embodiments, D5 can have a different diameter than D1 and D2. In some embodiments, diameter D5 can be from about 6 millimeters (mm) to about 40 mm. Diameter D5 can be from about 6, 8, 10, 12, 14, 16, 18, 20, 22, 24, 26, 28, 30, 32, 34, 36, 38 to about 40 mm. The third opening can be shaped and can be round, oval, rectangular or square.

The passive pawl includes a first end 148 and a second end 150, as shown in FIGS. 6 and 7. The first end is configured for engagement with slot 132. The passive pawl is configured to work in conjunction with a resilient member to control when the plunger is advanced during dispensing of the bone material and retracted after dispensing or reloading of the bone material. The passive pawl allows the plunger to be adjusted so that the plunger can be located adjacent to the bone material and if more bone material is added to the cannula, the plunger can be adjusted to be placed adjacent to the additional bone material. In this way, the bone material dispensing device can easily accommodate various quantities of bone material.

The passive pawl can pivot at an angle α4 of from about 2 to about 45 degrees, as shown in FIG. 7. In some embodiments, α4 is from about 1, 2, 4, 6, 8, 10, 12, 14, 16, 18, 20, 22, 24, 26, 28, 30, 32, 34, 36, 38, 40, 42, 44, 45 or from about 46 degrees.

The passive pawl includes a fourth opening 152 that is above and in alignment with the first opening and the second opening of the housing, and the third opening of the driving pawl, as shown in FIGS. 6 and 7. The fourth opening is configured to slidably receive at least a portion of the plunger, as described herein. The fourth opening can be centrally located on the passive pawl.

The fourth opening has a diameter D6, as shown in FIG. 7. D6 can be the same diameter as D1, D2 and D5, and has a greater diameter than plunger diameter D4. In some embodiments, D6 can have a different diameter than D1, D2 and D5. In some embodiments, diameter D6 can be from about 6 millimeters (mm) to about 40 mm. Diameter D6 can be from about 6, 8, 10, 12, 14, 16, 18, 20, 22, 24, 26, 28, 30, 32, 34, 36, 38 to about 40 mm. The fourth opening can be shaped and can be round, oval, rectangular or square.

The trigger assembly includes a second resilient member, such as a second spring 154 as shown in FIG. 2, that is configured for engagement with the passive pawl and a portion of the plunger, as described herein. The second spring is disposed on a portion of the plunger and between the second side 128 of the stationary handle and the passive pawl, as shown in FIGS. 2 and 6. The second spring comprises a proximal end 156 configured for engagement with an underside of the passive pawl and a distal end 158 which engages with the second side 128 of the stationary handle and the first opening 30 of the housing. The second spring is concentric with the fourth opening of the passive pawl and is concentric to the plunger. On moving the passive pawl toward the stationary handle, the second spring can be compressed and store energy, which will allow the plunger to be withdrawn or adjusted to allow bone material to be added to the cannula.

The trigger assembly includes a third resilient member, such as third spring 160 that is configured for engagement with the driving pawl, as described herein. The third spring is disposed concentric to the plunger and is disposed between a portion of the distal end of the housing and the driving pawl, as shown in FIGS. 6 and 7. The third spring comprises a proximal end 162 that engages with a distal surface of the driving pawl, and a distal end 164 that engages with the second opening 32 of the housing. At least a portion of the plunger is configured to be slidably received by the third spring, as described herein.

The folding cannula is similar to the foldable container found and fully described in U.S. application Ser. No. 15/581,817, of which is owned by Applicant and incorporated fully herein by reference. The folding cannula is configured to be loaded with the bone material and engages the funnel and/or the plunger for dispensing the bone material into a surgical site. The folding cannula comprises a proximal end 166 and a distal end 168. The folding cannula is segmented into an upper compartment 170 and a lower compartment 172, and the folding cannula is movable in a folded configuration and an unfolded configuration about a fold line 174.

The folding cannula has a diameter D7 that is smaller than a diameter of the funnel so as to allow at least a portion of the folding cannula to be held within the funnel, as shown in FIGS. 2 and 5. In some embodiments, diameter D7 can be from about 2 millimeters (mm) to about 40 mm. The diameter D7 can be from about 2, 4, 6, 8, 10, 12, 14, 16, 18, 20, 22, 24, 26, 28, 30, 32, 34, 36, 38 to about 40 mm. The folding cannula can have differing diameters throughout the folding cannula and does not have to have a uniform diameter.

In some embodiments, the proximal end of the folding cannula can have various geometries and sizes. In some embodiments, the proximal end of the folding cannula can be square, rectangular, round, plug, or disc shaped. The proximal end geometry of the folding cannula can have a diameter D9 that is larger than diameter D7 such that the proximal end geometry cannot pass the second opening 32 of the distal frame. In some embodiments, the diameter D9 can be from about 6, 8, 10, 12, 14, 16, 18, 20, 22, 24, 26, 28, 30, 32, 34, 36, 38 to about 40 mm.

Delivery Funnel

In some embodiments, the folding cannula engages with a delivery funnel 400 that is configured to removably engage the contact surface of the dispensing device, as shown in FIGS. 2, 6, 7 and 11. The delivery funnel 400, as shown in FIGS. 8-10, comprises a proximal portion 402, a distal portion 404 and a body 406. The distal portion includes a distal opening 405 and a distal tip 408. The distal tip may have various shapes, including circular, rectangular, polygonal. In some embodiments, the distal end of the funnel has a tip geometry, for example, a tip geometry that is indented to assist in the administration of the bone material to the surgical site. In some embodiments, the distal tip has a flange shape, in which the distal tip has a generally cylindrical profile with a middle section of the cylinder being an open space. The body of the delivery funnel has a passageway 442 extending along the entire body along a central axis CA from the proximal portion to the distal portion. The body has a proximal end 444, which joins the proximal portion of the funnel, and a distal end joins the distal tip of the funnel. The passageway allows the bone material to pass from the proximal portion through the body to the distal portion, where it is dispensed.

The proximal portion of the delivery funnel comprises a top end 410, a bottom end 424, and a body 448. The top end comprises a first holding surface 412, a second holding surface 414 and a third holding surface 416. The second holding surface is configured to receive a locking member of a bone material dispensing device. In some embodiments, the locking member has three contact surfaces forming n-shaped tongs such that the second contact surface 454 of the locking member is a groove receiving the second holding surface of the funnel. The holding surfaces have a generally rectangular profile across the width PW of the proximal portion. In some embodiments, the holding surfaces have a crescent shape with the thickest part pointing upward toward the locking member. The holding surfaces are aligned in series with the first holding surface closer to the proximal direction on the central axis of the dispensing device. In some embodiments, the first holding surface is an outer surface of the body of the proximal portion, which defines a top surface of a rectangular structure of the body. In some embodiments, the second holding surface is the only portion contacting the locking member. The third holding surface can be closer to the distal direction on the central axis while the second holding surface is in the middle. In some embodiments, the top end further comprises a guard protrusion 418 disposed on the second holding surface extending in a transverse direction relative to the central axis. In some embodiments, the guard protrusion comprises two guard protrusions disposed on two opposite ends of the second holding surface across the width of the proximal portion. The guard protrusions are configured to secure and stabilize the locking member once the locking member is received at the second holding surface. The guard protrusion stabilizes and defines the boundary of the locking member across the width of the funnel to ensure the locking member does not move about on the holding surface. In some embodiments, the two guard protrusions are disposed on the second holding surface, which mimic bat-like ears. The proximal portion further comprises a first edge 420 and a second edge 422 opposing the first edge across the width of the proximal portion. In some embodiments, the first holding surface is a top surface of a rectangular structure such that the structure has a side surface serving as a top contact surface 438. In some embodiments, the top contact surface is configured to contact the dispensing device or a holder 500. In another embodiment, the top contact surface does not contact any surface leaving a gap between the top contact surface and the dispensing device or the holder. The gap allows the top end of the funnel to be freely rotated without unnecessary friction when engaging the locking member. The bottom of the structure has a bottom edge 450 defining the bottom boundary of the top end.

The bottom end of the proximal portion comprises a rectangular-like structure and triangular-like structure. The top of the rectangular-like structure includes a side edge 428 and a top edge 426 defining the top boundary of the bottom end. The bottom end comprises a first tapered edge 430 and a second tapered edge 432 that extends toward the bottom boundary of the bottom end and joins at an apex 434 forming a triangular-like shape. The bottom end comprises a protrusion extending toward a proximal direction along a longitudinal direction to serve as a connector 436 configured to secure the funnel to a dispensing device or a holder. The protrusion is configured to be inserted into a corresponding opening on the dispensing device or on the holder. The connector is disposed adjacent to the apex. A side of the bottom end comprises a distal contact surface 440 configured to contact a dispensing device or the holder. When the connector is inserted into the dispensing device, it serves as an anchor or a pivot point for the funnel to rotate. When a user pushes the proximal end of the locking member in a downward direction, as shown by arrow EE in FIG. 6, the flange is moved in an upward position, as shown by arrow DD in FIG. 6. The flange of the locking member is in an unlocked position allowing the funnel to rotate around the connector and to slide the second holding surface to match the second contact surface of the locking member.

The bottom edge of the top end also defines a top boundary of the body of the proximal portion and the top edge of the bottom end also defines a bottom boundary of the body of the proximal portion. The body includes a generally flat plane and a proximal opening 403 configured to align with an opening in the dispensing device and receive at least a portion of a plunger. The proximal opening has a diameter DD1, which is the same as the widest opening of a proximal end 444 of the body of the delivery funnel. The proximal portion has a length PL across from the top end to the bottom end. When the funnel is in rotation via the connector, the rotation also allows the proximal opening to align with the second opening of the dispensing device.

The passageway 442 has a diameter DD2, which is smaller than DD1. The proximal end of the body has a generally conical shape comprising an inner surface 446 forming a slope. The dimension of the proximal end of the body and the proximal opening of the proximal portion are configured to facilitate the east of removal of a cannula from the funnel by hand. The dimension and the configuration also help avoid requiring forceps to pull the cannula out of the funnel. The slope and the central axis CA forms an angle α. The diameter of the proximal end has its widest part joining the proximal opening of the proximal portion and the size of the diameter diminishes toward the diameter of the passageway. The distal end of the body of the delivery funnel joins the distal portion of the delivery funnel at a ring of ledge 458. The ledge has a diameter DD3 smaller than DD1 and DD2. The ledge serves as a stop surface for loading the cannula. As the plunger exerts force onto the cannula in the funnel, the bone material inside the cannula can exit through the distal opening; meanwhile, the cannula can remain inside the funnel until removed by the user, where in some embodiments, it can be disposed.

In some embodiments, the angle α is from about 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, to about 90 degrees. In some embodiments, angle α is about 35 degrees.

In some embodiments, the funnel body is straight, having a cylindrical shape. The diameters DD1, DD2 and DD3 can be from about 2, 4, 6, 8, 10, 12, 14, 16, 18, 20, 22, 24, 26, 28, 30, 32, 34, 36, 38 to about 40 mm. The funnel has a length L2, which can be, for example, about 1 to about 20 inches. In some embodiments, the length of the funnel can be from about 1, 2, 3, 4, 5, 6, 7, 8, 9, 10, 11, 12, 13, 14, 15, 16, 17, 18, 19 to about 20 inches. In some embodiments, the funnel and the plunger are flexible. In some embodiments, the funnel and the plunger are rigid. In some embodiments, the plunger is more rigid that the funnel. In other embodiments, the funnel is more rigid than the plunger.

In some embodiments, the funnel locks with a portion of the distal end of the housing via the flange of the locking member and a front opening on the contact surface. In some embodiments, the funnel comprises a protrusion that allows mating and locking with the front opening, as described above. In some embodiments, the front opening is a detent that can be a catch, a lever, a spring, or a hinged catch that engages a notch of a ratchet, a protrusion, wall, or a combination thereof. The locking will allow the openings to align (as shown in FIGS. 6 and 7) and the plunger now can be slid through the openings. In some embodiments, the funnel can be entirely detachable and can snap onto the housing. In some embodiments, the funnel can be pivotably connected to the housing in a similar manner to a breech-loaded shotgun.

Dispensing Kit

The bone material dispensing system includes pusher 600, as described above and shown in FIGS. 1 and 11-14. The pusher is configured for inserting into the funnel to push out the bone material. In some embodiments, the pusher is also a dispensing device configured to deliver bone material through the funnel. The pusher is configured to receive force from a user via their hand or a tool such as a hammer. The pusher is configured to remove and/or dispense the bone material from the funnel and/or cannula. The pusher is configured to insert into the funnel from the proximal portion and/or the distal portion. In some embodiments, when the funnel is sitting on top of the holder, the pusher is inserted from the distal portion of the funnel as shown in FIG. 11. In some embodiment, the pusher is configured to insert in to the funnel from the proximal portion to deliver the bone material. In some embodiments, the funnel has its proximal portion sitting on a flat surface and the pusher is inserted through the distal end to push out the bone material.

Figure 17:
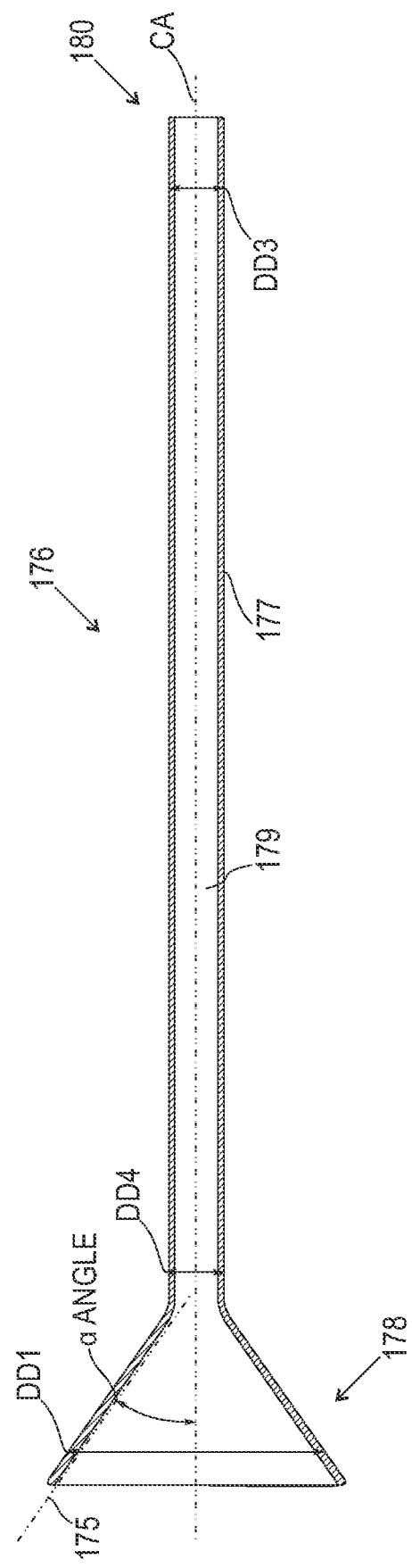
FIG. 17 is a cross-sectional view of another embodiment the funnel. The funnel includes a proximal end, a funnel body, a distal end and a longitudinal axis extending from the central axis of the proximal end to a center axis of the distal end. The proximal end has an inner slope which forms an angle with the longitudinal axis.
Figure 18:
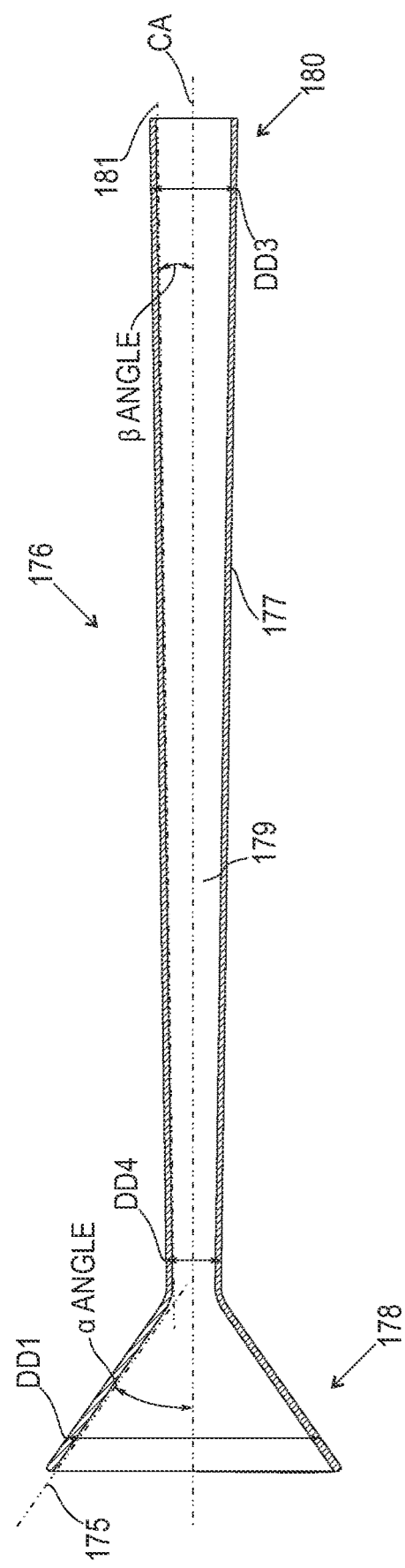
FIG. 18 is a cross-sectional view of another embodiment of FIG. 12. The funnel includes a tapered funnel body. The funnel body includes a proximal end having a diameter the same as the smallest diameter of the inner surface of the proximal end of the funnel. The funnel body includes a distal end having a diameter larger than the diameter of the proximal end of the funnel body.

In some embodiments, the funnel is a funnel 176 in FIGS. 17-18. A proximal end or a proximal portion 178 of the funnel can be inserted to deliver the bone material. In some embodiments, the proximal portion has a conical shape having a diameter DD1 formed by an inner surface of the proximal portion. The proximal portion has the largest diameter furthest away from a funnel body 177 of the funnel and the smallest diameter adjacent to the funnel body. A point on the largest diameter and a point on the smallest diameter forms a slope 175 along the inner surface of the proximal portion. The slope on the inner surface of the proximal portion forms an angle α with a central axis CA, which extends in the direction of the funnel passage from the proximal portion to the distal end 180 of the funnel, as shown in FIGS. 17 and 18.

In some embodiments, the angle α is from about 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, to about 90 degrees. In some embodiments, angle α is about 35 degrees.

In some embodiments, the distal end of the funnel has a tip geometry, for example, a tip geometry that is shaped or indented to assist in the administration of the bone material to the surgical site. In some embodiments, the funnel body is straight, having a cylindrical shape longer than a length of the proximal end of the funnel, as shown in FIG. 17. The diameter of the funnel body is the same from diameter DD4 of the funnel body's proximal end to diameter DD3 of the distal end of the funnel. FIG. 18 illustrates another embodiment of the funnel. In some embodiments, the funnel body is sloped or tapered, having a gradient with increasing diameters toward the distal end of the funnel forming a conical shape opposing the conical shape of the proximal end. The two opposing conical shapes having the smallest diameter DD4 jointly at a proximal end of the funnel body. The distal end has a diameter DD3, which is larger than DD4. In some embodiments, the diameter DD3 is smaller than the largest diameter of the proximal end of the funnel. The inner surface of the funnel body has a second slope 181 formed at an angle ß with a central axis CA, which extends in the direction of the funnel passage from the proximal end to the distal end of the funnel, as shown in FIGS. 17 and 18. In some embodiments, the distal end of the funnel has an inner surface having the second slope 181 forming the angle ß with a central axis CA.

In some embodiments, the distal end of the funnel comprises a ring of ledge. The ledge has a diameter DD3 smaller than DD1 and DD2. The ledge serves as a stop surface for loading the cannula. As the plunger exerts force onto the cannula in the funnel, the bone material inside the cannula can exit through the distal opening; meanwhile, the cannula can remain inside the funnel until removed by the user, where in some embodiments, it can be disposed.

The diameters DD1, DD3 and DD4 can be from about 2, 4, 6, 8, 10, 12, 14, 16, 18, 20, 22, 24, 26, 28, 30, 32, 34, 36, 38 to about 40 mm. In some embodiments, the angle ß is from about 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, to about 90 degrees. In some embodiments, the angle ß is less the angle α and/or less than 35 degrees. The funnel has a length L2, which can be, for example, about 1 to about 20 inches. In some embodiments, the length of the funnel can be from about 1, 2, 3, 4, 5, 6, 7, 8, 9, 10, 11, 12, 13, 14, 15, 16, 17, 18, 19 to about 20 inches.

Figure 13:
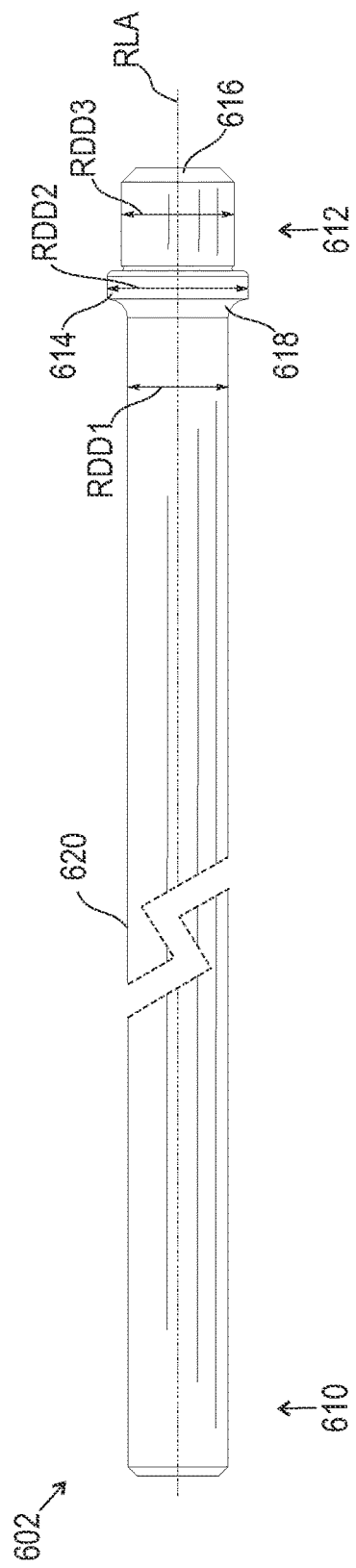
FIG. 13 is a side view of a dissembled shaft of the pusher in FIG. 1.
Figure 14:
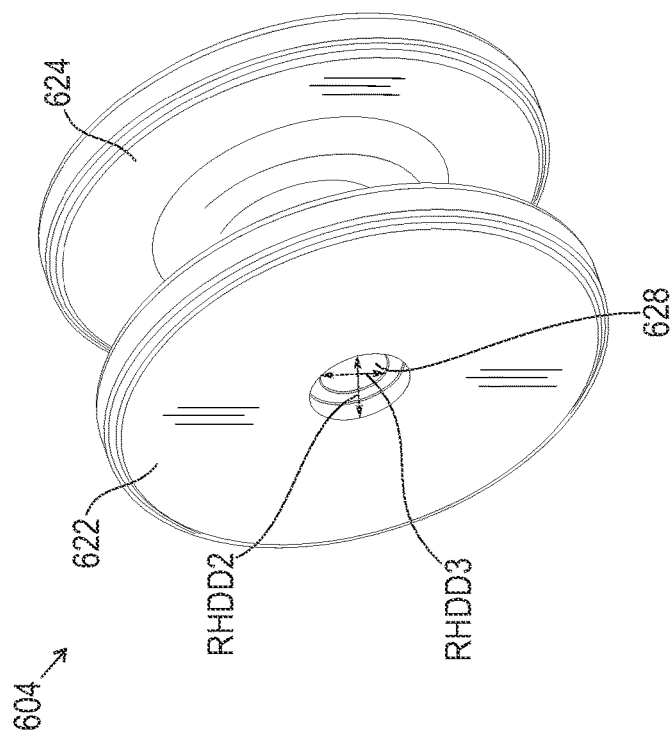
FIG. 14 is a perspective view of a dissembled head of the pusher in FIG. 1.

The pusher includes a shaft 602 and a head 604. The pusher also has a proximal portion 608 and a distal portion 606 extending along a longitudinal axis RLA. The shaft comprises a distal end 610, and proximal end 612 and a body 620. The body has a diameter RDD1. The proximal end of the shaft adjoins the head. The proximal end of the shaft has a ring 614 and a tip 616. The tip has a diameter RDD3 and is configured to fit and connect to the head such that the head encloses the tip completely. The ring has a diameter RDD2 and is also configured to fit and connect to the head such that the head only partially encloses the ring. The shaft also has a tapered ring 618 joining the ring and the shaft body. It is noted that RDD2 is greater than RDD3, which is greater than RDD1. The tapered ring has a gradually decreasing diameter between RDD2 and RDD1, as shown in FIG. 13. The head has 3 portions including a holder ring 622 disposed closer to the distal portion on the longitudinal axis. The holder ring is configured to provide a rest surface for a user's finger or a gripping tool. A gripping ring 626 is adjacent to the holder ring and has a diameter smaller than the holder ring. The gripping ring is configured to provide structure and to receive a load of force. A loading ring 624 is adjacent to the gripping ring and is disposed in the proximal direction. The loading ring is configured to provide a surface for a user to exert the force, via a head or other tool, including a hammer. In some embodiments, the loading ring has a generally flat profile. In some embodiments, the loading ring has a crescent curve which conforms ergonomically to a human palm. The head further comprises an opening 628 for a shaft to be inserted and securely connected to the head. The opening of the head and the tip of the shaft may be threadedly connected or snap-fitted. The opening has a diameter RHDD2 corresponding to the diameter of the ring of the shaft and a diameter RHDD3 corresponding to the diameter of the tip of the shaft allowing the shaft and the head to connect together.

Figure 16:
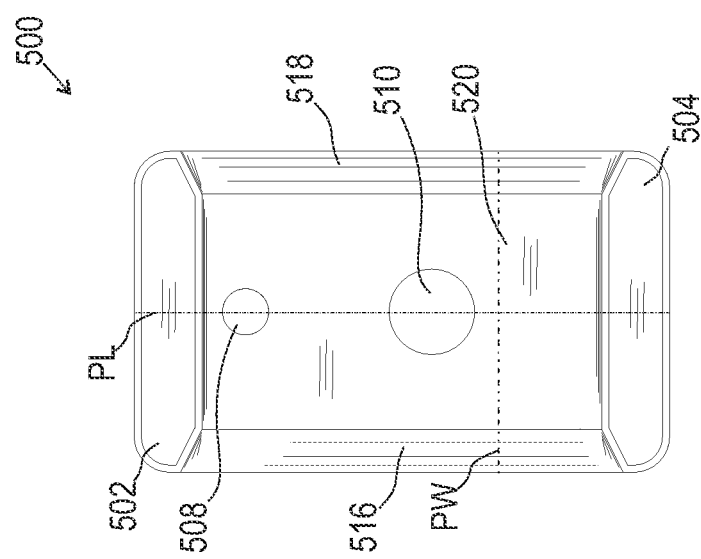
FIG. 16 is a bottom view of the holder in FIG. 1.
Figure 15:
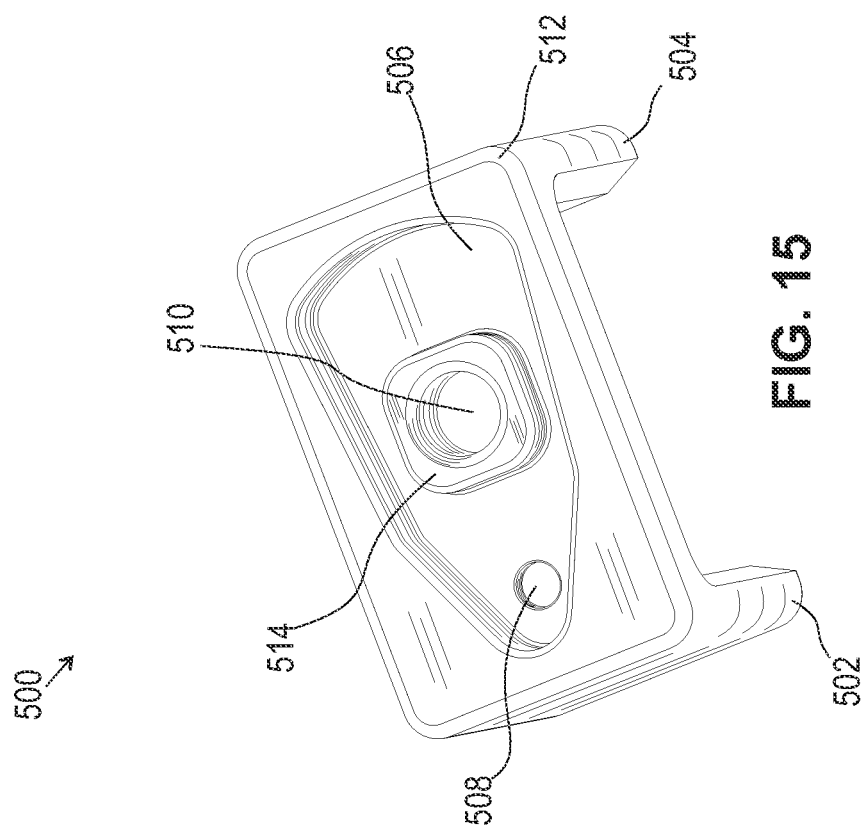
FIG. 15 is a perspective view of the holder in FIG. 1.

The bone material dispensing system includes holder 500, as described above and shown in FIGS. 1 and 15-16. The holder is configured to provide a stabilized surface for the funnel and to withstand an impact when a force is exerted to push the bone material out of the funnel. The holder is configured to have a surface, which conforms to the shape of the proximal portion of the funnel. The holder is configured to receive a force from a user via their hand or a tool such as a hammer.

The holder includes a support and a platform. A support includes a first support 502 and a second support 504. In some embodiments, the supports are rectangularly structured providing legs to the plane. The platform includes a perimeter 512 defining the boundaries of the holder, a contact surface 506 configured to receive the proximal portion of the funnel, and an island 514 protruding from the contact surface. The contact surface is disposed on a platform plane 520, which is a depression having a depth from a topmost point of the perimeter of the holder to the platform plane. The depression depth is configured to further stabilize the funnel when it sits on the contact surface. The contact surface also includes tapered edges and an apex matching the tapered edges and the apex of the funnel. The contact surface has a first opening 508 configured to receive a protrusion from the funnel. The island comprises a second opening 510 configured to align with the proximal opening of the funnel. The platform has a length PL and a width PW. The platform has a first tapered edge 516 extending along the length of the platform and a second tapered edge 518 opposing the first tapered edge across the width. The tapered edges of the platform are tapered along the depression depth.

In operation, the folding cannula is loaded with the bone material and inserted into the proximal end of the funnel so that at least a portion of the folding cannula is held within the funnel and at least a portion of the folding cannula is fed through the proximal opening of the funnel. The funnel is then locked onto the housing via the locking member, as shown in FIG. 7 when the user places the locking member in the locking position or downward position, as shown by arrow BB.

In some embodiments, the funnel is configured to be unlocked/released from the bone material dispensing device by the user in vivo. The unlocking/release of the funnel in vivo allows the user to remove the folding cannula while the funnel is still attached to the bone material dispensing device via a protrusion or a connector and without having to remove the funnel from the patient. This reduction in potential trauma or damage to soft tissues, particularly nerves, during funnel placement is beneficial. Unlocking/release of the funnel in vivo also reduces the number of steps required in a surgical procedure.

In some embodiments, the bone material dispensing device can be used in conjunction with the products found and fully described in U.S. application Ser. Nos. 15/340,770 and 15/818,395; and U.S. Publication Nos. 2017/0216051, 2018/0078385, 2017/0216045, 2018/0071113, and 2016/0100955, of which are all owned by Applicant and incorporated fully herein by reference. In some embodiments, various orthopedic implants can be used in conjunction with the bone material dispensing device.

In some embodiments, the folding cannula can be made of a memory shape polymer and/or alloy to allow the folding cannula to move from an unfolded configuration to a folded configuration without the need for a locking mechanism. Memory shape polymers include, but are not limited to polyethers, polyacrylates, polyamides, polysiloxanes, polyurethanes, polyethers amides, polyurethane/ureas, polyether esters, polynorborene, cross-linked polymers such as cross-linked polyethylene and cross-linked poly(cyclooctene), inorganic-organic hybrid polymers, and copolymers such as urethane/butadiene copolymers, styrene-butadiene copolymers. Memory shape alloys include, but are not limited to TiNi, CuZnAl, and FeNiAl alloys. In some embodiments, the folding cannula can be fabricated by, but not be limited to, injection molding of plastic materials comprising rigid, surgical grade plastic and/or metal materials.

In some embodiments, components of the bone material dispensing system may be made from materials, such as for example, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or combinations thereof. The folding cannula, funnel portion or plunger may optionally include one or more tapered regions. In various embodiments, these components may be blunt, beveled, diamond point, ball tip, trocar tip, etc. These components may also have a tip style vital for accurate treatment of the patient depending on the surgical site. Examples of tip styles include, for example, Trephine, Cournand, Veress, Huber, Seldinger, Chiba, Francine, Bias, Crawford, deflected tips, Hustead, Lancet, or Tuohey. In some embodiments, the bone material dispensing device and tray can be made from materials that allow the bone material dispensing device to be reusable, or alternatively made from materials that allow for a single, disposable use.

In some embodiments, the shape of the folding cannula may be selected for particular applications. Such shape and configuration may include, for example, the basic shape of a folding cannula (e.g., a tubular shaped cannula).

Methods

A method of dispensing a bone material is provided. The method comprises loading a bone material dispensing device with the bone material, the bone material dispensing device comprising a housing having a frame comprising an opening configured to slidably receive at least a portion of a plunger, a locking member pivotably connected to the housing, the locking member comprising a locking surface extending adjacent to the housing configured to engage a surface of a funnel, the frame comprising a contact surface and a front opening configured to engage a funnel; engaging a connector of the funnel with the front opening of the frame and the locking member being movable in a locking position, such as a downward position to lock the surface of the funnel to the housing, aligning the funnel with the frame and the funnel configured to receive at least a portion of the plunger to dispense the bone material.

In some embodiments, the method comprises loading a bone material dispensing device via loading the bone material into a cannula, inserting the loaded cannula into a funnel, connecting the funnel to the bone material dispensing device, locking the funnel to the bone material dispensing device, pushing a plunger of the bone material dispensing device into the funnel such that the bone material exits out of the funnel into a target site. In some embodiments, the bone material is loaded into the funnel directly without a cannula. In some embodiments, the method of implanting bone material comprises adding the bone material into the funnel and/or a cannula. In some embodiments, the funnel is connected to the bone material dispensing device prior to the cannula being inserted into the funnel. In some embodiments, the plunger may receive resistance from the bone material, the funnel and/or the cannula during the operation. A remediate operation is conducted in such scenario.

In some embodiments, the bone material dispensing device can be employed to unlock the funnel but still remains attached to the funnel and the cannula is removed and replaced with another loaded cannula. In some embodiments, a pusher is inserted into the funnel to push the bone material out of the funnel. In some embodiments, the bone material dispensing device is removed from the funnel completely and a pusher is inserted into the funnel to push the bone material out of the funnel. In some embodiments, the funnel is configured to be unlocked from the bone material dispensing device by the user. In some embodiments, the funnel is placed onto a holder. When placing the funnel onto a holder, the top contact surface and the bottom contact surface of the funnel are placed to contact the contact surface of the holder. The contact surface of the holder is a depression from the holder's perimeter such that the depth secures the funnel in place. In operation, the proximal opening of the funnel is aligned with the second opening of the holder and the connector of the funnel is aligned to fit into the first opening of the holder. Once the proximal portion of the funnel is secured to the holder in an upright position such that the distal portion of the funnel is facing upward. The pusher is inserted into the funnel from the distal portion of the funnel and it is configured to push the bone material out of the proximal opening of the funnel and the second opening of the holder onto a surface. A new cannula can be placed into the funnel and the funnel can be reattached and locked with the bone material dispensing device to continue the delivery.

In some embodiments, the bone material can be dispensed in a quantifiable, controlled and predefined amount of from about 0.25 cc to about 1 cc. The bone material may be dispensed in a quantifiable, controlled and predefined amount of from about 0.25, 0.30, 0.35, 0.40, 0.45, 0.50, 0.55, 0.60, 0.65, 0.70, 0.75, 0.80, 0.85, 0.90, 0.95 to about 1 cc. In some embodiments, the bone material can be dispensed in a quantifiable, controlled and predefined amount of from about 0.25 oz to about 1 oz. The bone material may be dispensed in a quantifiable, controlled and predefined amount of from about 0.25, 0.30, 0.35, 0.40, 0.45, 0.50, 0.55, 0.60, 0.65, 0.70, 0.75, 0.80, 0.85, 0.90, 0.95 to about 1 oz.

The bone material can be mixed with liquid material and optionally a therapeutic agent until a desired consistency of the bone material is achieved (e.g., putty, paste, etc.). The bone material can be mixed with a suitable diluent and then loaded. The folding cannula may have enough space to allow for the bone material and a volume of diluent to be mixed. In some embodiments, the diluent includes dextrose, other sugars including but not limited to, sucrose, fructose, glucose, lactated ringer's, polyols including, but not limited to, mannitol, xylitol, sorbitol, maltitol, lactitol, polysaccharides including but not limited to native or pre-gelatinized starch, maltodextrins, cyclodextrins, mineral compounds including, but not limited to, dicalcium or tricalcium phosphate, either dihydrate or anhydrous, cellulose derivatives including, but not limited to, microcrystalline cellulose, lactose, either monohydrates thereof or anhydrous, as well as their mixtures such as dicalcium phosphate dihydrate, mannitol, pre-gelatinized maize starch, microcrystalline cellulose and their mixtures, water and/or NaCl (saline). In some embodiments, the saline is 0.90% saline or 0.45% saline. In some embodiments, other delivery vehicles can be used for example, D5W (dextrose in 5% water), D5NS (dextrose in 5% water and normal saline) and D5W/1/2NS (D5W and ½ normal saline), blood, mesenchymal stem cells, or the like.

The fourth compartment may include a container for holding the bone material and/or a vial for holding any other instruments needed for the delivery. A fifth compartment may include gloves, drapes, wound dressings and other procedural supplies for maintaining sterility of the implanting process, as well as an instruction booklet, which may include a chart that shows how to administer the bone material after mixing it. A sixth compartment may include the spatula, needles, additional devices and/or sutures. Each tool may be separately packaged in a plastic pouch that is sterilized. A seventh compartment may include an agent for radiographic imaging. A cover of the kit may include illustrations of the dispensing/administering procedure and a clear plastic cover may be placed over the compartments to maintain sterility.

In various embodiments, one or more components of the bone material dispensing system is sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

In various embodiments, gamma radiation is used in the terminal sterilization step, which involves utilizing ionizing energy from gamma rays that penetrate deeply into the bone material dispensing device. Gamma rays are highly effective in killing microorganisms, they leave no residues, nor do they have sufficient energy to impart radioactivity to the apparatus. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the bone material dispensing device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize the bone material dispensing system including, but not limited to, gas sterilization such as, for example, with ethylene oxide or steam sterilization.

The bone material dispensing system can be used to treat a variety of conditions including osteoporosis, bone fracture repair or healing, dental procedures for which increased bone formation in the jaw is of clinical benefit, repair of craniofacial bone defects induced by trauma or congenital defects such as cleft palate/lip, and a number of other musculoskeletal disorders where native bone growth is inadequate, which will be evident to those of ordinary skill in the art. The bone material can be administered to treat open fractures and fractures at high risk of non-union, and in subjects with spinal disorders, including subjects in need of spinal fusion (e.g., anterior lumbar interbody fusion, posterior lumbar spinal fusion, and cervical spine fusion) or subjects having degenerative disc disease or arthritis affecting the lumbar and cervical spine.

Bone Material

In some embodiments, the bone material can be demineralized bone material. The demineralized bone material can comprise demineralized bone, powder, chips, granules, shards, fibers or other shapes having irregular or random geometries. These can include, for example, substantially demineralized, partially demineralized, or fully demineralized cortical and cancellous bone. These also include surface demineralization, where the surface of the bone construct is substantially demineralized, partially demineralized, or fully demineralized, yet the body of the bone construct is fully mineralized. The configuration of the bone material can be obtained by milling, shaving, cutting or machining whole bone as described in, for example, U.S. Pat. No. 5,899,939. The entire disclosure is herein incorporated by reference into the present disclosure.

In some embodiments, the bone material can comprise elongated demineralized bone fibers having an average length to average thickness ratio or aspect ratio of the fibers from about 50:1 to about 1000:1. In overall appearance the elongated demineralized bone fibers can be round, spherical, granular, elongated, powders, chips, fibers, cylinders, threads, narrow strips, thin sheets, or a combination thereof. In some embodiments, the bone material comprises elongated demineralized bone fibers and chips. In some embodiments, the bone material comprises fully demineralized fibers and surface demineralized chips. In some embodiments, the ratio of fibers to chips or powders is from about 5, 10, 15, 20, 25, 30, 35, 40, or 45 fibers to about 30, 35, 40, 45, 50, 55, 60, 65, or 70 chips.

In some embodiments, the bone material comprises demineralized bone matrix fibers and demineralized bone matrix chips in a 30:60 ratio. In some embodiments, the bone material comprises demineralized bone matrix fibers and demineralized bone matrix chips in a ratio of 25:75 to about 75:25 fibers to chips.

In some embodiments, the bone material can be an inorganic material, such as an inorganic ceramic and/or bone substitute material. Exemplary inorganic materials or bone substitute materials include but are not limited to aragonite, dahlite, calcite, brushite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, BIOGLASS™ fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), or combinations or derivatives thereof.

In some embodiments, the bone material can comprise mineral particles, which comprise tricalcium phosphate and hydroxyapatite in a ratio of about 80:20 to about 90:10. In some embodiments, the mineral particles can comprise tricalcium phosphate and hydroxyapatite in a ratio of about 70:30 to about 95:5. In some embodiments, the mineral particles can comprise tricalcium phosphate and hydroxyapatite in a ratio of about 85:15.

In some embodiments, the bone material may be seeded with harvested bone cells and/or bone tissue, such as for example, cortical bone, autogenous bone, allogenic bones and/or xenogeneic bone while it is mixed.

In some embodiments, the bone material may be mixed with one or more therapeutic agents, for example, an anti-inflammatory agent, an analgesic agent, an osteoinductive growth factor, an antimicrobial agent or a combination thereof. Osteoinductive agents include one or more members of the family of Bone Morphogenetic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-14 (GDF-5), BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

Indeed, the osteoinductive factors are the recombinant human bone morphogenetic proteins (rhBMPs) because they are available in unlimited supply and do not transmit infectious diseases. In some embodiments, the bone morphogenetic protein is a rhBMP-2, rhBMP-4, rhBMP-7, or heterodimers thereof. Recombinant BMP-2 can be used at a concentration of about 0.4 mg/mL to about 10.0 mg/mL, preferably about 1.5 mg/mL.

The bone material may include or be mixed with one or more members from the TGF-β superfamily. For example, the matrix may include AMH, ARTN, GDF1, GDF10, GDF11, GDF15, GDF2, GDF3, GDF3A, GDF5, GDF6, GDF7, GDF8, GDF9, GDNF, INHA, INHBA, INHBB, INHBC, INHBE, LEFTY1, LEFTY2, MSTN, NODAL, NRTN, PSPN, TGFB1, TGFB2, TGFB3, FGF, basic FGF, VEGF, insulin-like growth factor, EGF, PDGF, nerve growth factor or combinations thereof.

The bone material may include or be mixed with a therapeutic agent including, but not limited to, IL-1 inhibitors, such Kineret® (anakinra), which is a recombinant, non-glycosylated form of the human interleukin-1 receptor antagonist (IL-1Ra), or AMG 108, which is a monoclonal antibody that blocks the action of IL-1. The bone material may include or be mixed with therapeutic agents including excitatory amino acids such as glutamate and aspartate, antagonists or inhibitors of glutamate binding to NMDA receptors, AMPA receptors, and/or kainate receptors. The bone material may include or be mixed with therapeutic agents to reduce inflammation including but not limited to interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), or aurin-tricarboxylic acid (which inhibits TNF-α).

The bone material may include or be mixed with a therapeutic agent including, but not limited to, an analgesic agent. Examples of analgesic agents include, but are not limited to, acetaminophen, tramadol, lidocaine, bupivacaine, ropivacaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, levorphanol, meperidine, methadone, morphine, nalbuphine, opium, oxycodone, papaveretum, pentazocine, pethidine, phenoperidine, piritramide, dextropropoxyphene, remifentanil, sufentanil, tilidine, tramadol, codeine, dihydrocodeine, meptazinol, dezocine, eptazocine, flupirtine or a combination thereof.

The bone material may include or be mixed with a therapeutic agent including, but not limited to, an anti-inflammatory agent. An example of an anti-inflammatory agent includes, but is not limited to, clonidine, sulindac, sulfasalazine, naproxen, diclofenac, indomethacin, ibuprofen, flurbiprofen, ketoprofen, aclofenac, aloxiprin, aproxen, aspirin, diflunisal, fenoprofen, mefenamic acid, naproxen, phenylbutazone, piroxicam, meloxicam, salicylamide, salicylic acid, desoxysulindac, tenoxicam, ketoralac, clonidine, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, fenamates (mefenamic acid, meclofenamic acid), nabumetone, celecoxib, etodolac, nimesulide, apazone, gold, tepoxalin; dithiocarbamate, or a combination thereof.

Anti-inflammatory agents also include steroids, such as for example, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, dexamethasone 21-acetate, dexamethasone 21-phosphate di-Na salt, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide or a combination thereof.

The bone material may include or be mixed with a therapeutic agent including, but not limited to, a statin. Examples of a useful statin include, but are not limited to, atorvastatin, simvastatin, pravastatin, cerivastatin, mevastatin (See U.S. Pat. No. 3,883,140; the entire disclosure is herein incorporated by reference), velostatin (also called synvinolin; see U.S. Pat. Nos. 4,448,784 and 4,450,171; these entire disclosures are herein incorporated by reference), fluvastatin, lovastatin, rosuvastatin and fluindostatin (Sandoz XU-62-320), dalvastain (EP Application Publication No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin.

In some embodiments, the bone material can include an antimicrobial agent. In some embodiments, the antimicrobial agent can include one or more of triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol-9, fusidic acid, cephalosporins, or combinations thereof.

Examples of antimicrobial agents include, by way of illustration and not limited to, acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; chlorhexidine, cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; ganciclovir and ganciclovir sodium; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin and oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillins such as penicillin g benzathine, penicillin g potassium, penicillin g procaine, penicillin g sodium, penicillin v, penicillin v benzathine, penicillin v hydrabamine, and penicillin v potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin b sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; to sufloxacin; trimethoprim; trimethoprim sulfate; trisulfapyrimidines; troleandomycin; trospectomycin sulfate; tyrothricin; vancomycin; vancomycin hydrochloride; virginiamycin; zorbamycin; or combinations thereof.

The antimicrobial agent in the bone material can be an antiviral agent that can be mixed with the bone material. Antiviral agents can include, but are not limited to, vidarabine, acyclovir, famciclovir, valacyclovir, gancyclovir, valganciclovir, nucleoside-analog reverse transcriptase inhibitors (such as AZT (zidovudine), ddI (didanosine), ddC (zalcitabine), d4T (stavudine), and 3TC (lamivudine)), nevirapine, delavirdine, protease inhibitors (such as, saquinavir, ritonavir, indinavir, and nelfinavir), ribavirin, amantadine, rimantadine, neuraminidase inhibitors (such as zanamivir and oseltamivir), pleconaril, cidofovir, foscarnet, and/or interferons.

Although the invention has been described with reference to embodiments, persons skilled in the art will recognize that changes may be made in form and detail without departing from the spirit and scope of the disclosure.

What is claimed is:

1. A bone material dispensing system comprising a tubing having a proximal portion and a distal portion, the tubing configured to dispense a bone material, the proximal portion having a wider diameter than the distal portion, the proximal portion configured to engage a bone material dispensing device, the proximal portion comprising a top end and a bottom end, the top end opposite the bottom end, wherein the bottom end comprises a first tapered edge and a second tapered edge joining at an apex, and the bottom end also comprises a connector, the connector of the bottom end being adjacent to the apex such that when the connector secures the tubing to the bone material dispensing device, the connector becomes a pivot point to allow the tubing to rotate about the connector.

2. The bone material dispensing system of claim 1, wherein the top end comprises a surface having a protrusion, the protrusion comprising two protrusions disposed on two opposite ends of the surface of the top end across a width of the proximal portion.

3. The bone material dispensing system of claim 2, wherein the two protrusions are in contact with an outside surface of a locking member of the bone material dispensing device such that the two protrusions stabilize the locking member.

4. The bone material dispensing system of claim 3, wherein the surface comprises a crescent shape pointing upward toward the locking member.

5. The bone material dispensing system of claim 3, wherein the protrusion extends along a direction transverse to a central axis of the tubing.

6. The bone material dispensing system of claim 1, wherein the connector of the bottom end extends along a central axis of the tubing.

7. The bone material dispensing system of claim 1, wherein the proximal portion comprises a body portion disposed between the top end and the bottom end, the body portion having an opening configured to receive a cannula and/or a plunger.

8. The bone material dispensing system of claim 7, wherein the cannula comprises a folding cannula.

9. The bone material dispensing system of claim 8, wherein the folding cannula has a diameter smaller than a diameter of the opening of the tubing so as to allow at least a portion of the folding cannula to be held within the tubing.

10. The bone material dispensing system of claim 1, wherein the tubing comprises a tubing body adjacent to the proximal portion of the tubing.

11. The bone material dispensing system of claim 10, wherein the tubing body has a proximal end and a distal end, the proximal end and distal end each having a diameter, the diameter of the proximal end being larger than the diameter of the distal end, the proximal end being adjacent to the proximal portion of the tubing.

12. The bone material dispensing system of claim 11, wherein the proximal end has a generally conical shape having an inner surface and a decreasing diameter toward the tubing body.

13. A bone material dispensing system comprising a bone material dispensing gun comprising a housing having a proximal end, a distal end, and a longitudinal axis, the proximal end having a first opening and the distal end having a second opening, the first opening and the second opening configured to slidably receive at least a portion of a plunger; and a tubing disposed at the distal end of the housing, the tubing having a proximal portion, the proximal portion comprising a top end and a bottom end, the top end opposite the bottom end; a pusher having a shaft and a head, the shaft having a diameter smaller than a diameter of the tubing body and at least a portion of the pusher configured to slidably move within the tubing; and a holder configured to receive the proximal portion of the tubing, wherein the bottom end comprises a first tapered edge and a second tapered edge joining at an apex.

* * * * *